US007738946B2

(12) United States Patent
Thurston et al.

(10) Patent No.: US 7,738,946 B2
(45) Date of Patent: Jun. 15, 2010

(54) SYSTEM, METHOD AND APPARATUS FOR THE DETECTION OF PATIENT-BORNE FLUORESCING MATERIALS

(75) Inventors: Marlin O. Thurston, Columbus, OH (US); Helen Thurston, legal representative, Columbus, OH (US); Karl W. Olson, Worthington, OH (US)

(73) Assignee: Actis, Ltd., Columbus, OH (US)

( * ) Notice: Subject to any disclaimer, the term of this patent is extended or adjusted under 35 U.S.C. 154(b) by 382 days.

(21) Appl. No.: 11/906,706

(22) Filed: Oct. 3, 2007

(65) Prior Publication Data

US 2008/0281208 A1    Nov. 13, 2008

Related U.S. Application Data

(63) Continuation-in-part of application No. 11/801,549, filed on May 10, 2007.

(51) Int. Cl.
*A61B 6/00* (2006.01)
*A61B 8/00* (2006.01)
(52) U.S. Cl. ................ 600/477; 600/431; 424/9.6
(58) Field of Classification Search ........ 600/431, 600/436, 476, 477; 250/336.1; 422/82.07, 422/82.08, 82.11; 436/172; 435/7.1, 7.25; 424/9.6; 356/300
See application file for complete search history.

(56) References Cited

U.S. PATENT DOCUMENTS

| | | | | |
|---|---|---|---|---|
| 4,782,840 A | * | 11/1988 | Martin et al. | 600/431 |
| 4,801,803 A | * | 1/1989 | Denen et al. | 250/336.1 |
| 4,889,991 A | * | 12/1989 | Ramsey et al. | 250/336.1 |
| 4,893,013 A | * | 1/1990 | Denen et al. | 250/336.1 |
| 5,151,598 A | * | 9/1992 | Denen | 250/336.1 |
| 6,259,095 B1 | * | 7/2001 | Bouton et al. | 250/336.1 |
| 2009/0234225 A1 | * | 9/2009 | Martin et al. | 600/431 |

* cited by examiner

*Primary Examiner*—Eric F Winakur
*Assistant Examiner*—Michael T Rozanski
(74) *Attorney, Agent, or Firm*—Mueller Smith & Okuley, LLC

(57) ABSTRACT

System, method and apparatus wherein a probe employing non-imagining optics is utilized in conjunction with a fluorescing (e.g., nanocrystal) tracer at the body of a patient. Excitation components within the probe working end are utilized to excite the nanocrystals to fluoresce at wavelengths in the near infrared region, such fluorescent energy is homogenized by interacting with involved tissue to provide a uniform fluorescing intensity over the surface of a photo-detector. Initialization and background determination procedures are described along with a technique for determining statistically significant levels of fluorescing activity.

7 Claims, 13 Drawing Sheets

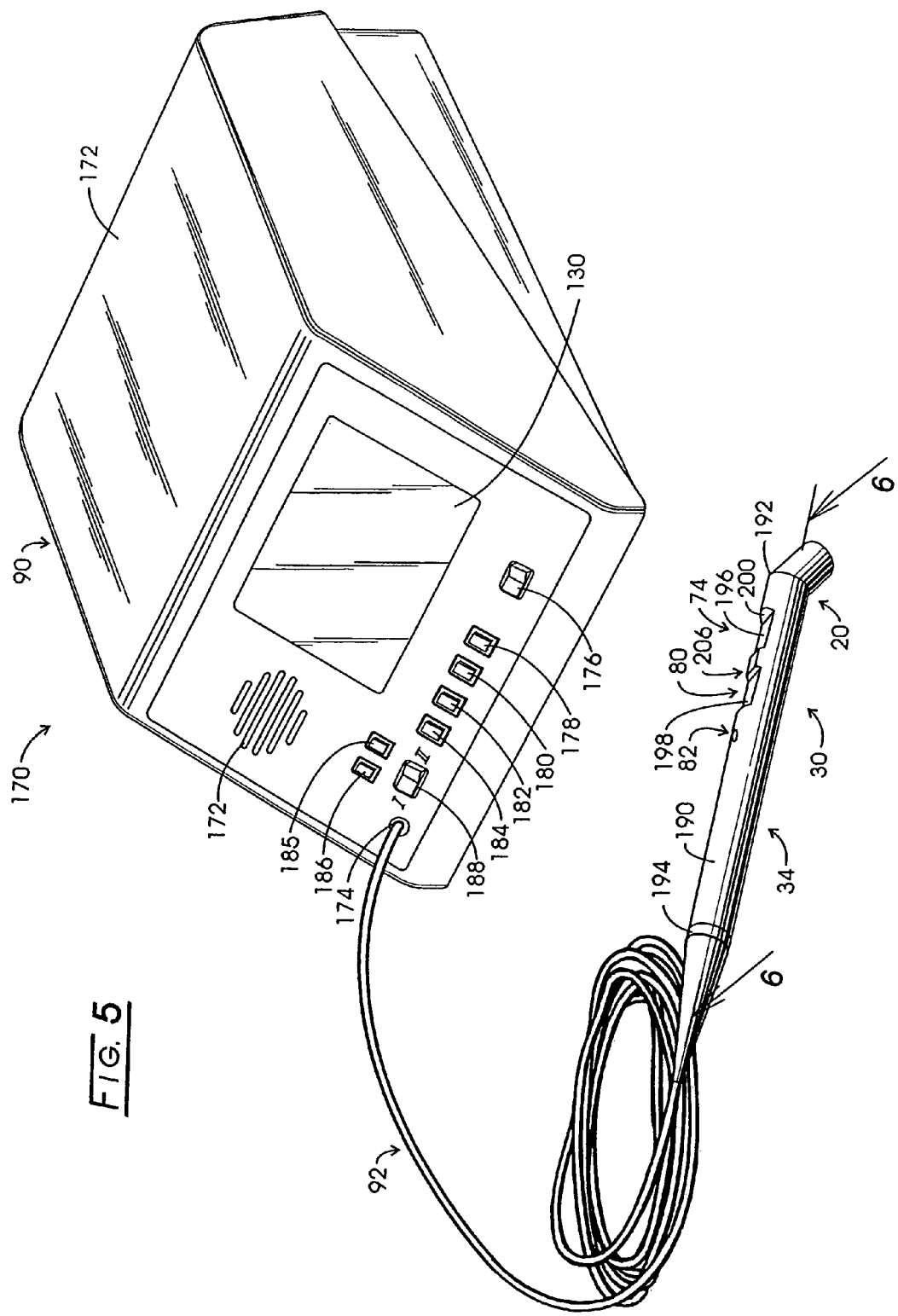

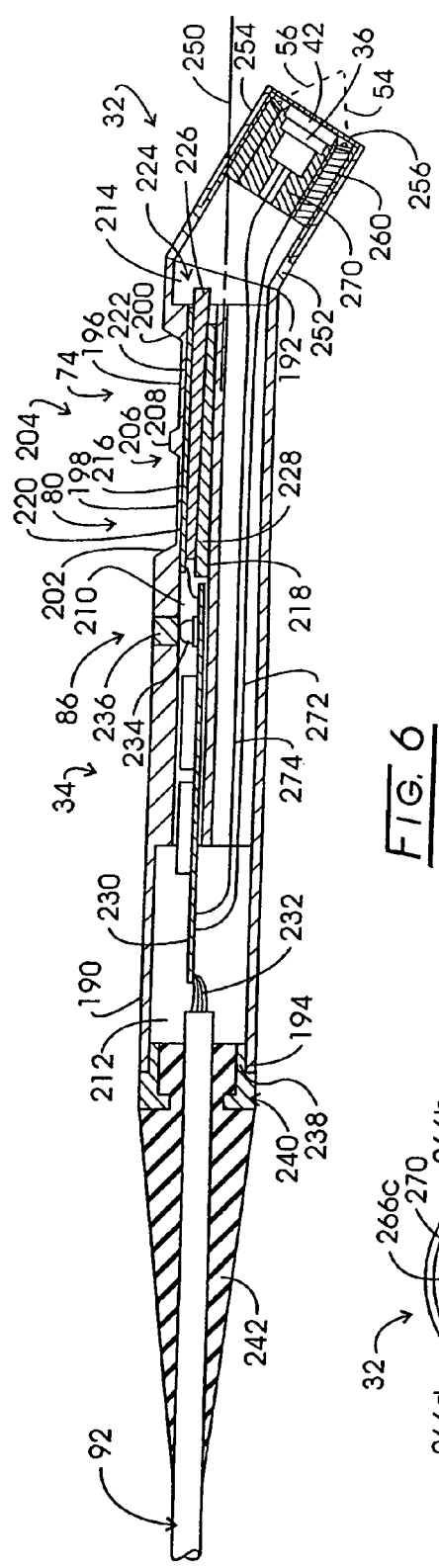

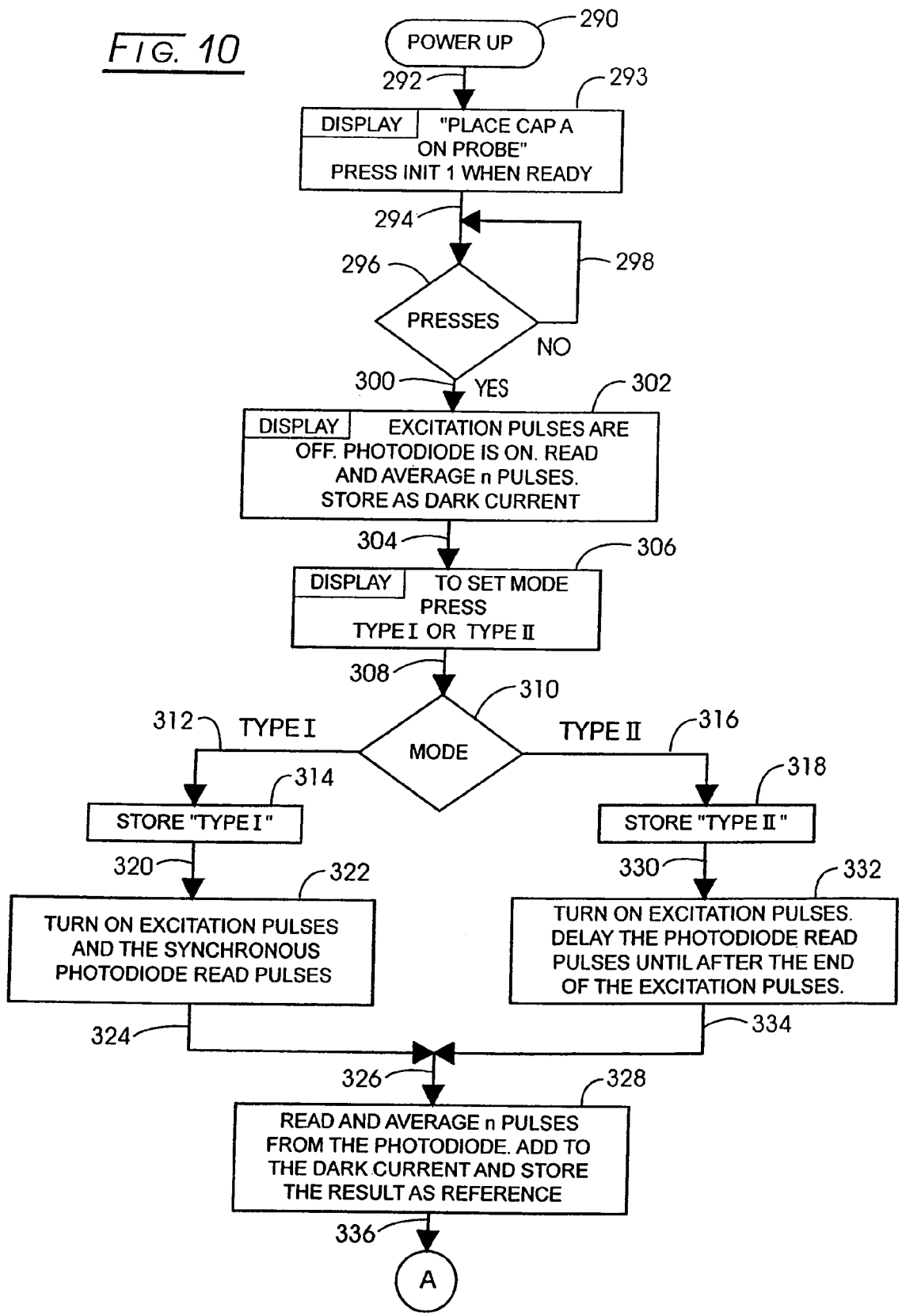

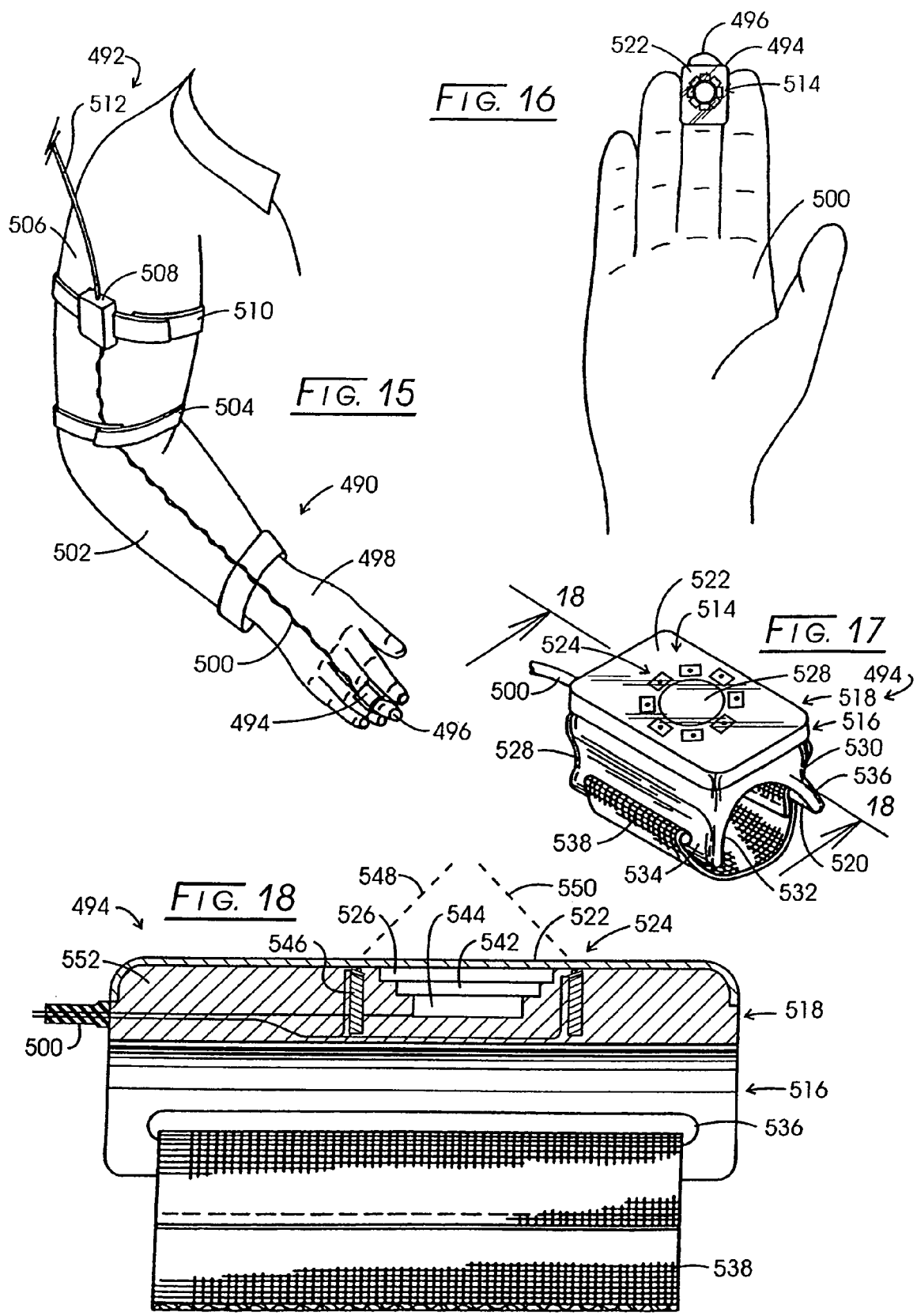

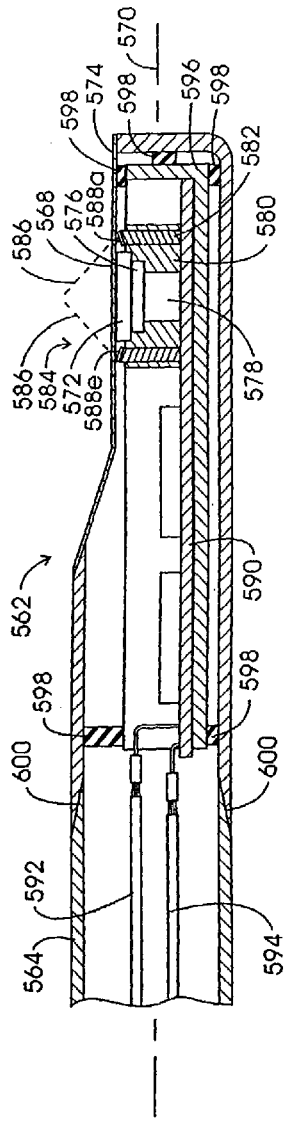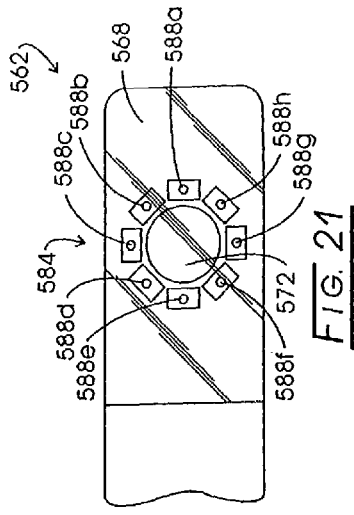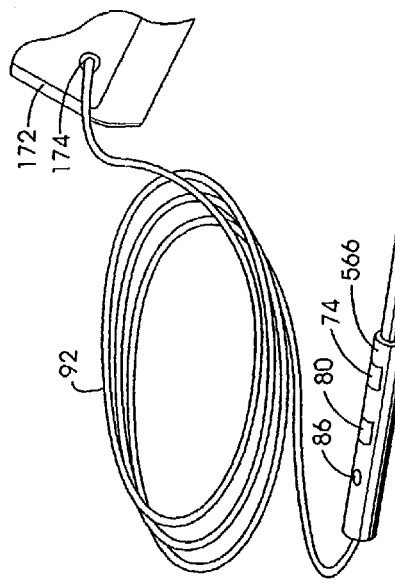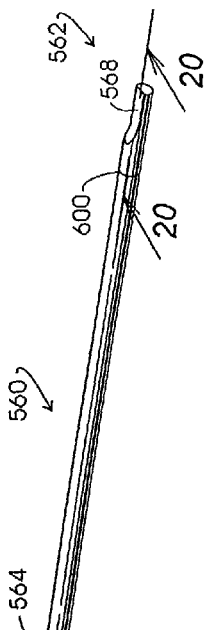

SYSTEM, METHOD AND APPARATUS FOR THE DETECTION OF PATIENT-BORNE FLUORESCING MATERIALS

CROSS-REFERENCE TO RELATED APPLICATIONS

This application is continuation-in-part of application Ser. No. 11/801,549, filed on May 10, 2007, the disclosure of which is expressly incorporated herein by reference.

STATEMENT REGARDING FEDERALLY SPONSORED RESEARCH

Not applicable.

BACKGROUND

In about 1983, a surgical oncologist, E. W. Martin, Jr., M.D. and a physicist-electrical engineer, M. O. Thurston, Ph.D. combined their talents to explore then perceived deficiencies in the treatment of colorectal cancer. Why did it recur? Investigators then opined that some tumor was "missed" in surgery in that it was not located by pre-operational imaging, intra-operative visualization or palpation. Such hidden neoplastic tissue was referred to as "occult" tumor and was considered to be an important aspect of the recurrence of cancer and lessoning of patient survivability. The Martin-Thurston approach at that time was to radio-label an antibody specific to the tumor, inject it prior to surgery, then carry out surgery using current surgical protocols, whereupon a hand-held probe radiation detector was used intra-operatively to scan the surgical site for occult tumors. Early studies showed the necessity of delaying this surgery following the injection of locator or radiolabeled antibodies. That delay permitted the labeled antibody to preferentially concentrate at neoplastic tissue as well as to permit normal body function based reduction of background radiation. This procedure is described in U.S. Pat. No. 4,782,840 by Martin, Jr. and Thurston entitled "Method for Locating, Differentiating, and Removing Neoplasms", issued Nov. 8, 1988. The procedure was referred to as "radio immunoguided surgery" or "RIGS®".

The evolution of the hand-held probe and its associated control system was not a trivial endeavor, requiring extensive research. In this regard, the system was required to distinguish the totally random and spontaneous isotopic emissions of occult tumor from the same form of totally random isotopic background emissions. For a variety of important reasons, $^{125}$I was elected as the radioisotope label of choice, having a half-life of about sixty days. Concerning the randomness of an isotope, from a given point in time, an atom of $^{125}$I might emit a photon after five minutes from a starting point and another emission might occur a year later. The sixty day half-life is an average (the time required for the rate of such emissions to decrease to one half). A successful control approach for differentiating neoplastic tissue from background was statistically based upon count rate. The basis of that statistical control is described by Ramsey and Thurston in U.S. Pat. No. 4,889,991 entitled "Gamma Radiation Detector with Enhanced Signal Treatment", issued Dec. 26, 1989.

Returning to the $^{125}$I radiolabel, studies carried out by Dr. Thurston showed that to accommodate the RIGS procedure with the necessary generally multi-week waiting period permitting body clearance of background radiation, a relatively longer half-life isotope having no high energy component and a dominant low energy was called for. $^{125}$I was essentially the only isotope with characteristics suitable for the RIGS procedure. However, both patients and health care personnel were not entirely receptive to working with or being injected with this radioactivity. While the sixty-day half-life of $^{125}$I fulfilled the waiting interval needs, it posed problems among others, with respect to regulatory agency requirements. Radioactive material, including anything contaminated with it must be protectively stored for a period amounting to ten times its half-life. Thus, for the case of $^{125}$I, the storage interval became six hundred days, a time element considered quite burdensome. Notwithstanding its lower energy characteristic (27 Kev) the emissions from this labeling isotope could inflict damage upon associated antibodies during shelf life. Thus, about one out of each six antibodies was labeled.

During the formative years of the RIGS system, the locators or antibodies, which were radiolabeled, were specific to the neoplasm or tumor itself. As these materials were improved, the locators developed were specific to tumor-associated cell surface antigens. The term "cell surface antigen" refers to an antigen of the plasma membrane proper and to any part of the tumor cell periphery, including the extracellular matrix. Most of the antigens demonstrated on the surface of cells have been chemically defined as polysaccharides, glycoproteins, glycolipids or proteins. A high molecular weight (200,000-400,000) tumor associated glycoprotein, called TAG-72, is present in 85% of colorectal cancers although there is considerable heterogeneity in its expression in the primary tumor, lymph nodes, and distant metastasizes. TAG-72 occurs widely on human carcinoma cells, including certain human breast carcinoma cell lines, but is absent in normal healthy adult tissues, except secretory-phase endometrium. One of the first antibodies of this type used with the RIGS system was called B72.3.

Colorectal adenocarcinomas have their genesis in mucin-secreting cells. Colon cancer occurs in the lining of the colon, which has to be coated at a rather high rate with mucin both for lubrication and digestive juice protection purposes. The epithelial cells involved reproduce at a very high rate. When such cells transform to cancer cells, they continue to secrete mucin but such mucin is distinctly different from mucin produced from non-malignant cells. It was found that TAG antibodies were capable of binding to these abnormal mucins called sialomucins, to locate or indicate the presence of cancer cells.

A variety of monoclonal antibodies reactive with human gastrointestinal carcinoma evolved. Of particular note, were the monoclonal antibodies (MAb) CC49 (ATCC CRL9459) and CC83 (ATCC CRL9453) developed by Schlom and coworkers at the National Cancer Institute. These antibodies exhibit increased reactivity to antigen-positive tissue, reflecting a higher affinity. See U.S. Pat. No. 5,512,443.

Essentially, hundreds of surgical procedures were carried out by surgeons employing the RIGS system in conjunction with sialomucin binding locators, such as CC49 and CC83. During this period E. W. Martin, Jr. and associating surgeons detected "probe positive" (locator bound sialomucin) lymph nodes. It may be recalled that the locators are specific to a by-product of tumor as opposed to tumor itself. Generally, these lymph nodes were readily accessible with the RIGS probe, being present along, for example, the aorta, vena cava or near the liver. Notwithstanding the controversy necessarily involved in removing lymph structure, these probe-positive lymph nodes were directed to pathology along with the resected tumor burden. The generally received response was that the dissected nodes were hyperactive but no presence of cancer cells was detected. The issue as to the appropriateness of removing these probe-positive lymph nodes remained essentially unresolved until patient survival data was evolved.

Data collected with respect to patients having had probe-positive lymph nodes removed indicated what has been called "remarkable" survival improvement. An analysis was subsequently carried out with respect to the question as to whether a small number of malignant cells in a lymph node would be readily detected by frozen section techniques. Assuming a spherical node of 0.5 cm diameter, an examination of the entire node in six-micron sections would require over 800 sections with a total area of 1600 cm$^2$. The likelihood of observing malignant cells would have been, at best, remote. See the following publication:

1. Barbera-Guillen, et al., "First Results for Resetting the Anti-Tumor Immune Response by Immune Corrective Surgery in Colon Cancer" *Am. J. Surg,* 1998,176:339-343.

In the early 1990s investigators utilized the RIGS system to locate, differentiate and stage other types of cancer, for instance, endocrine tumors involved, inter alia, with breast, children, gastrinomas, lung and nervous system. Generally, the approach was to administer a radiolabeled somatostatin congener to assess the patient with the RIGS probe. However, before subjecting the patient to such administration, an initial determination preferably was made as to whether the radiolabeled somatostatin congener would bind to the tumor site, i.e., whether somatostatin receptors are associated with the neoplastic tissue. This was conveniently done with a wide variety of endocrine tumors, which release peptides or hormones, referred to as "biochemical markers." In order to make this determination, initially a biochemical marker-inhibiting dose of unlabeled somatastatin congener was administered to the patient. The biochemical marker associated with the neoplastic tissue then was monitored to determine whether the administered somatostatin congener reduces the presence of the marker in the patient. If the monitored presence of the marker was reduced, then the surgeon could be confident that the neoplastic tissue or tumor contains receptors to which the somatostatin would bind. Thus, the administration of radiolabeled somatostatin congener was appropriate for such patient. If the biochemical marker associated with the neoplastic tissue was not appropriately reduced following the administration of the unlabeled somatostatin congener, then the neoplastic tissue may not be determinable by the use of radiolabeled somatostatin congener and alternative modalities of treatment would be considered, such as the use of radiolabeled antibodies.

See: O'Dorisio, et al., U.S. Pat. No. 5,590,656; entitled "Application of Peptide/Cell Receptor Kinetics Utilizing Radiolabeled Somatostatin Congeners in the In Situ, In Vivo Detection and Differentiation of Neoplastic Tissue"; issued Jan. 7, 1997 and incorporated herein by reference.

For a variety of reasons, the use of the RIGS system was suspended and oncologists have no technique available for detecting cancer inducing lymph nodes. In consequence, the survival rates for patients having undergone tumor-burden removal associated with colonic cancers have generally descended to pre-RIGS levels.

BRIEF SUMMARY

The present disclosure is addressed to system, method, and apparatus wherein an intra-operative probe structured with non-imaging optics is employed in concert with a locator incorporating a fluorescing material and which specifically binds a marker produced by or associated with neoplastic tissue. With the method, lymph tissue associated with neoplastic antigen becomes detectible and, thus, removable, opening an opportunity to return to the patient survival rates achieved with the earlier RIGS system.

The probe apparatus, structured with non-imaging objects is capable of medical uses beyond cancer therapy. A working end of the probe is configured having a photo-detector, such as a photodiode, with an associated pre-amplification stage, a longpass filter functioning to block excitation and ambient wavelengths, and an encapsulating assembly with a forwardly disposed transparent window having a forward transmission surface contactable with tissue. Because near infrared returning fluorescing energy is scattered by tissue, its intensity becomes uniform or is homogenized to achieve reliable intensity-based detector output.

The system at hand is one wherein the operator is prompted from a control console display to carry out necessary initialization procedures involving a small dark chamber created by a cap extendable over the probe working end. This cap is configured with an internal forward surface formed of a tissue emulating polymeric material. As a first initialization procedure the cap is positioned over the probe working end, the photo-detector is enabled and dark current/electronic noise is detected and its value is stored. A second initialization then ensues with the energization of the excitation (LED) components and enablement of the photo-detector to measure the intensity of back scattered excitation illumination, which will be in the red region of the spectrum. The sum of these photo-detector values both during initialization and subsequent scanning becomes a stored reference value, which is subtracted from scan values. Such control is dependent upon the type of fluorescing material being used, the photo-detector being enabled in synchronization with the energization of the excitation components for a Type I nanocrystals (or other fluorescing material). Where a Type II nanocrystal, for example, is used, there is a random delay between the time of excitation of a crystal and the subsequent emission of a fluorescence photon. For a large number of nanocrystals, the rate of emission is a decreasing exponential function of the time after excitation with a time constant of the order of a microsecond. For this type fluorescing nanocrystal, the photo-detector is enabled for a sampling interval subsequent to the interval of excitation and total fluorescing intensity is computed, for example, by a convolution procedure.

Another initialization procedure, which, in effect, is a calibration approach, also is carried out with a light-type cap carrying a Type I or Type II fluorescing nanocrystals or other material. With the cap in place, the excitation components are energized and the photo-detector is enabled in appropriate sequence to obtain an intensity readout. That readout then is compared by the operator with a readout value located on the outside of the cap.

When the system is employed in conjunction with a locator, which incorporates a fluorescing material (or fluorescing agent) and specifically binds a marker produced or associated with neoplastic tissue, the patient is injected with such locator and a clearance interval ensues. For certain preferential locators, that clearance interval may be about two to three weeks to permit a substantial diminution of that locator which does not bind a marker. At the time of surgery, the probe is moved across normal tissue to obtain a background level of fluorescence. The system then computes a statistically significant threshold above mean background to determine when the transmission surface of the probe is over cancer involved tissue. In general, the threshold will be three standard deviations over mean background, such a three sigma value being selected because the expected probability of a false positive reading would be less than 1%.

The probe-based system may be employed with a generally cylindrical hand graspable support extending to an angularly disposed working end. Additionally, the system may be employed with a finger mounted support, which slides over a finger of a surgeon. A third support is intended for laparoscopic surgery wherein the working end components are mounted so as to be "side looking" and supported from an elongate accessing tube.

Another aspect of the disclosure is to provide a method for the surgical treatment of patients afflicted with neoplastic tissue, which includes the steps of:
  (a) administering to a patient an effective amount of a locator incorporating a fluorescing material and which specifically binds a marker produced by or associated with neoplastic tissue;
  (b) permitting time to elapse following step (a) for the locator to preferentially concentrate at any marker and for unbound locator to be cleared so as to increase the ratio of fluorescing-based radiation from specifically bound locator to fluorescing-based radiation representing background in the patient;
  (c) after the clearing time has elapsed in step (b) surgically accessing an operative field of the patient;
  (d) providing a hand manipulative probe having forwardly disposed excitation components energizable to cause any material to fluoresce at a detection wavelength or wavelengths and a forwardly disposed photo-detector configured for response to non-imaged detection wavelengths so as to develop detection outputs corresponding with fluorescing radiation intensity;
  (e) using the probe, determining and storing the fluorescing radiation intensity at the background;
  (f) based upon the fluorescing radiation intensity at the background, determining a statistically significant fluorescent radiation intensity value whereat a perceptible cue is generated;
  (g) removing tumor burden from the patient using the probe where necessary to locate and differentiate neoplastic tissue; and
  (h) using the probe, determine and remove lymph tissue sites exhibiting detection outputs.

Other aspects of the disclosure will, in part, be obvious and will, in part, appear hereinafter. The disclosure accordingly, includes the system, apparatus, and method possessing the construction, combination of elements, arrangement of parts and steps that are exemplified in the following detail description.

For a fuller understanding of the nature and aspects hereof, reference should be made to the following detailed description taken in connection with the accompanying drawings.

BRIEF DESCRIPTION OF THE DRAWINGS

FIG. 5 is a perspective view of the present system showing a control assembly console, probe and associated cable;

FIG. 6 is a sectional view of an probe taken through the plane 6-6 shown in FIG. 6;

FIG. 6A is an enlarged partial view of the working end of the probe of FIG. 6;

FIG. 7 is a front view of the working end of the probe of FIG. 6;

FIG. 8 is a perspective view of an initialization cap employed with the system of the invention;

FIG. 9 is a sectional view taken through the plane 9-9 shown in FIG. 8;

FIG. 10 is flow chart illustrating an initialization procedure;

FIG. 15 is a perspective view of a surgeon's hand, arm and shoulder showing the mounting of a finger supported intra-operative probe;

FIG. 16 is a front view of a surgeon's hand showing an intra-operative probe, which is finger mounted;

FIG. 17 is a perspective view of a finger-supported intra-operative probe;

FIG. 18 is a sectional view taken through the plane 18-18 shown in FIG. 17;

FIG. 19 is a perspective view of a probe configured for laparoscopic utilization;

FIG. 20 is a sectional view taken through the plane 20-20 in FIG. 19; and

FIG. 21 is a top view of the working end of the probe of FIG. 19.

DETAILED DESCRIPTION

In the discourse to follow, three charts initially are presented illustrating about ten year survival probability data with respect to colorectal cancer patients having undergone surgery, which utilized the RIGS procedure. The discussion then turns to nanocrystals as illustrative of fluorescing agents, which may be excited to fluoresce and function to supplant the radiolabel employed with the RIGS procedure. In this regard, the instant system utilizing such nanocrystal technology then is described in conjunction with block diagrams, an illustration of the working end of a probe and a system involving a probe, control assembly console and initialization chambers or caps. Flow charts concerning two initialization routines and scan routines are then described in conjunction with two modulation timing diagrams concerning two nanocrystal implementations. Lastly, finger-mounted and laparoscopic probe structures are illustrated and described. Much of the disclosure will be illustrated by specific reference to nanocrystals; however, such illustration is not a limitation on the disclosure, as additional fluorescing materials also will be disclosed herein.

Figure 1:
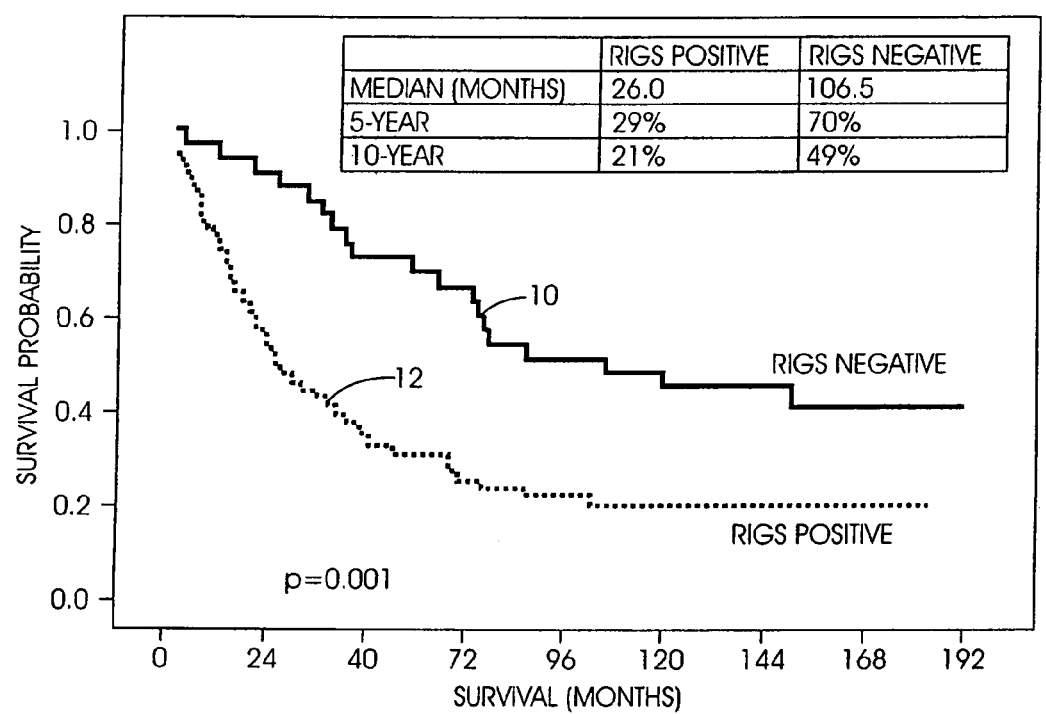
FIG. 1 is a colon cancer patient survival probability chart resulting from the utilization of prior radio immuno-guided surgery with respect to stages I through IV.

To gain an insight into the utilization of cancer detection systems such as the earlier-described RIGS approach, reference is made to FIG. 1, which plots the survival probability against time in months for a population of 83 patients who had undergone surgery using the RIGS approach. The plots, in effect, represent life expectancy, drops in the curves being the result of the death of patients from any cause. For example, in addition to cancer occasioned deaths, deaths could be from heart attacks, strokes, auto accidents, and the like. The data includes all Stages I through IV of the cancer involvement. In this regard, Stage I involves an early and preliminary detection of cancer and as the stages increase in number, cancer involvement becomes more extended until Stage IV, which fundamentally is considered a terminal condition. Where the RIGS system indicated that all cancer involved tissue including that in the lymph system was removed, then the cases are considered to be "RIGS negative" and their survival probability is represented at curve 10. On the other hand, there were conditions wherein the RIGS probe would show a continued presence of cancer but under conditions, for example, involving vital tissue where all indications of cancer could not be removed and the condition was considered to be "RIGS positive". This RIGS positive condition is plotted at curve 12. The median survival in months with respect to curve 12 for RIGS positive patients was 26.0. Correspondently, the median survival in months for RIGS negative patients as represented at curve 10 was 106.5 months or about 8.9 years. The probability factor, p, for curves 10 and 12 was 0.001, representing a statistical reliability of about 1 in 1000, which is an excellent value. The curves further show that five year survival was 29% with respect to RIGS positive patients and 70% with respect to RIGS negative patients. At 10 years, curve 12 reveals the probability of 21% survival with respect to RIGS positive patients and curve 10 represents a 10 year probability of survival of 49% with respect to RIGS negative patients.

Figure 2:
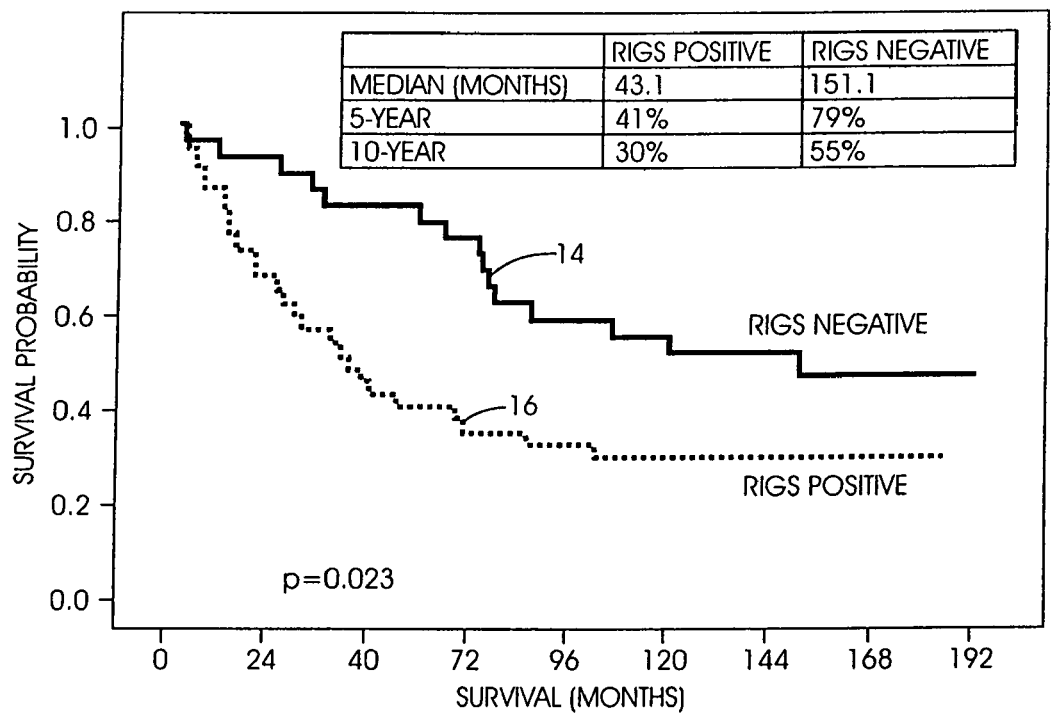
FIG. 2 is a chart similar to FIG. 1 but showing colon cancer patient survival probability for stages I and II only.

Turning to FIG. 2, similar survival probability data is charted but with respect to Stages I-II only. Curve 14 charts survival probability for patients deemed RIGS negative with respect to months, while curve 16 plots survival probability for patients having been deemed RIGS positive where RIGS identified cancer involvement remained after surgery. The median probability of survival with respect to curve 16 and RIGS positive patients was 43.1 months, while the median probability in months for the survival of RIGS negative patients was 151.1 months or about 12½ years. As before, the deaths could be for any cause but cancer deaths are included. The five year probability of survival with respect to curve 16 was 41% and the corresponding five year survival with respect to curve 14 was 79%. At ten years the probability of survival with respect to curve 16 was 30% and by contrast, the probability of survival with respect to curve 14 was 55%. The probability factor, p, for curves 14 and 16 was 0.023, which remains a good value.

Figure 3:
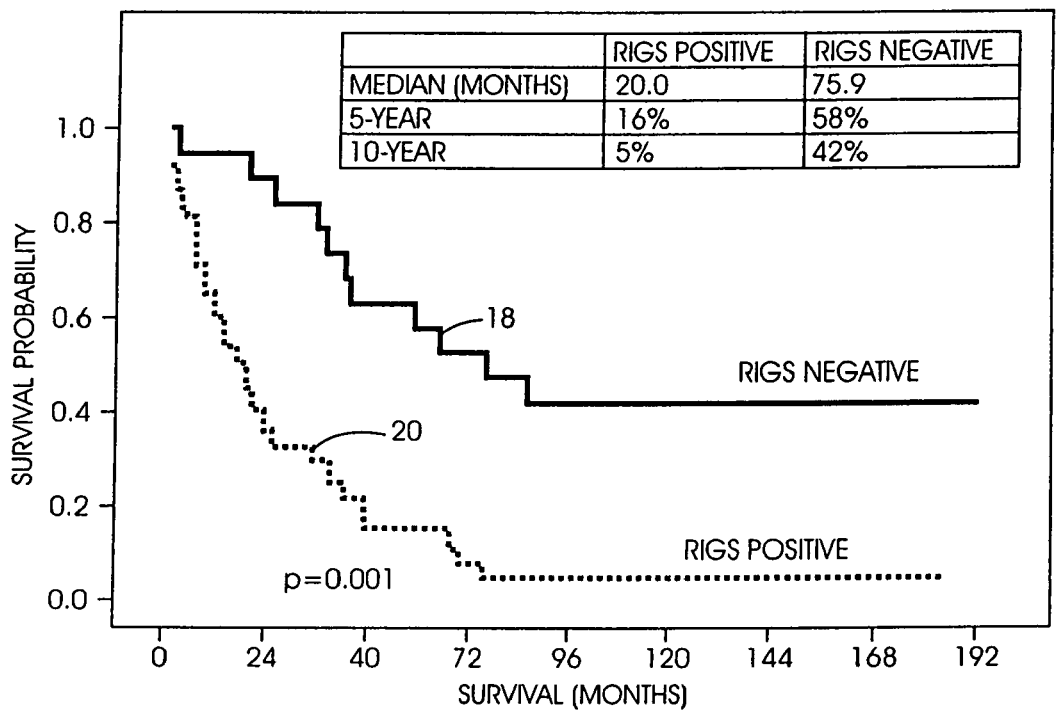
FIG. 3 is a colon cancer patient survival probability chart similar to FIG. 1 but including only patients at stages III and IV.

Lastly, looking to FIG. 3, a similar chart is provided but in this case, with respect to patients having been deemed at Stages III or IV. Curve 20 represents that the median number of months probability of survival was 20.0 while, correspondently, the mean probability for survival of patients represented at curve 18 was 75.9 months or about 6.3 years. The five year probability of survival with respect to curve 20 was 16% and the corresponding five year survival probability for curve 18 was 58%. At ten years, the probability of survival from deaths of any cause as represented at curve 20 was 5% and the corresponding ten year probability for survival with respect to curve 18 was 42%. The probability factor, p, for curves 18 and 20 was 0.001. As is apparent, providing a viable intra-operative cancer detection technique will be most beneficial.

Semiconductor nanocrystals are gaining popularity due to the ability of industry to tailor their optical and energetic properties by varying the size, shape, and material parameters. Quantum confinement of charged carriers in nanocrystals to sizes comparable to their excitonic Bohr radius results in discrete energy levels and narrow optical transitions. Nanocrystals enjoy a broad range of applications ranging from biological imaging, quantum computing, and solar cells to electroluminescent devices.

Two types of nanocrystals are incorporated with the instant system. A first type employs fluorescent nanocrystals such as CdSe, CdTe (CdX). With these fluorescent nanocrystals, the emission of a photon is delayed from the time of absorption of an excitation photon by a random time interval of about 10 nanoseconds. The crystals are designed to fluoresce in the near infrared region of the spectrum to enhance transmission through tissue. In this same regard, the nanocrystals are excited by photons at a higher energy level, i.e., photons with a shorter wavelength. In general, again looking to transmission through tissue, excitation energy preferably will be in the red region of the spectrum. The nanocrystals are arbitrarily designated herein as a Type I. A discussion of water-soluble functionalized nanocrystals of the CdX variety is set forth in U.S. Pat. No. 6,114,038 by Castro, et al., entitled "Functionalized Nanocrystals and Their Use in Detection Systems", issued Sep. 5, 2000, and incorporated herein by reference. Reference also is made to the following publication:

2. Castro, S., "Biopixal Nanocrystalline Fluorescent Markers", *Genetic Engineering News*, Vol 19, No. 17, Oct. 1, 1999.

A second approach for developing a fluorescing locator is through the utilization of a family of PbS nanocrystals that are coated with a thin layer of a dielectric compound. When a photon of excitation is absorbed by a this type fluorescent nanocrystals, the emitted photon has a random delay constraint or time that is of the order of a microsecond. Accordingly, where there is a modulation of the excitation energy, for example, in the form of short pulses, the fluorescence will continue in exponential decaying fashion after the excitation has stopped. To use this effect, the reading or sampling pulse is started a short time after the excitation pulse ends and a total fluorescing intensity is computed with a convolution approach. These nanocrystals are arbitrarily designated herein as a Type II. See the following publication:

3. Warner, et al., "Time-Resolved Photoluminescence Spectroscopy of Ligand-Capped PbS Nanocrystals", *Nano-Technology* 16 (2005) 175-179.

The use of excitation energy in the red region of the spectrum in combination with fluorescence in the near infrared region is attractive particularly with respect to identifying lymph nodes retaining locators in the course of colorectal surgery. These nodes are relatively small, generally only about 3 mm in diameter and they are close to the surface. Accordingly, the spectrum at hand is one capable of being useable at depths of 2 cm and 3 cm, which is entirely adequate. Studies undertaken during the years of utilization of the RIGS system developed criteria of sensitivity for detecting such lymph nodes. Investigators were able to calculate the number of atoms of radioactive iodine, which were in the lymph nodes. It turned out that the nodes contained about 300 million atoms of iodine and associated antibodies. For practical reasons, the number of antibodies was greater than the number of iodine atoms and affected lymph nodes showed a RIGS or isotopic radiation count of about 10 counts per second over background, a condition requiring rather significant statistical analysis. However, this situation alters with the use of nanocrystals fluorescing in the near infrared region. In this regard, about 300 million or so small fluorescent nanocrystals will be located in a node, all of which may be excited repeatedly. By contrast, once an iodine atom has radiated, it becomes tellurium and no longer usable in the detection process. With the nanocrystal approach, theoretically, with respect to a given affected lymph node, a billion photons per second may be generated. The instant system, may, for example, excite at a shorter wavelength of about 650 nanometers to achieve a nanocrystal fluorescence in the order of 700 nanometer wavelengths. For both excitation and fluorescing response there will be some degree of reduction of signal strength. This reduction comes about from the absorption of radiation by tissue. In this regard, such absorption primarily will be a result of the water content of the tissue and is not as significant as the scattering of photons as they pass through or impinge upon tissue. Such scattering results in a reduction of signal strength and of blurring, the latter result being advantageous inasmuch as the receiving optics are non-imaging, in effect, a Lambertion radiation intensity distribution being desirable over the face of a photo detector.

See the following publication with respect to non-imaging optics:

4. Winsron, et al., "Non-imaging Optics", Elsevier Academic Press, Boston Mass., 2005.

By employing a non-imaging optical system, as opposed to an imaging one, the surface of a photo-detector will receive fluorescing photon radiation, which is both directly confrontational but also evolves from very shallow angles occasioned by significant scattering in tissue. Sensitivity is substantially improved over an imaging optical system.

With respect to other fluorescing materials, traditional fluorescent dyes and their derivatives, such as, for example, fluorescein, rhodamine, bisbenzimide, and DAPI, are organic molecules that contain aromatic rings. Chemistries that functionalize these molecules for coupling to biological molecules must be developed on a case-by-case basis. Fluorescent dyes are sensitive to the surrounding environment, and decreases in fluorescence intensity can be brought about by changes, for example, in media pH, solvents, and dissolved oxygen. Such dyes are light-sensitive and must be handled under subdued illumination to prevent photobleaching. The excitation spectrum of typical organic fluorophores is quite narrow, necessitating the need to employ separate excitation wavelengths for each marker. The emission spectrum of these fluorophores is relatively broad.

CyDye™ fluorophores (referred to as the cyanines, Amersham Biosciences) are designed for use in high throughput screening and in fluorescence-based detection assays. CyDyes are particularly suited as fluorescent probes since their red to near infrared absorption and emission maxima (500-800 nm) are distinguishable from the shorter wavelength endogenous autofluorescence associated with biological materials (tissue) and equipment. Other characteristics of CyDyes that make them good candidates for use in the disclosed fluorescence detection schemes include their relatively narrow bandwidths (in the range of 60-70 nm); photostability (CyDyes (Cy5, Cy5.5, Cy7) have demonstrated good photostability for periods of 30-60 minutes in biological use, which time period may be sufficient for present purposes); aqueous solubility; "Favorable" fluorescent quantum yields (measure of the intensity of the emitted fluorescence); good pH stability; and non-cytotoxicity (CyDyes are derived from indocyanine green (ICG), a tricarbocyanine dye that is water-soluble and has been approved for in vivo use in medical testing and imaging). Cy 7, for example, emits in the 745-750 nm range.

Additional fluorescent materials are under development that similarly may find use in in vivo applications disclosed herein.

Figure 4A:
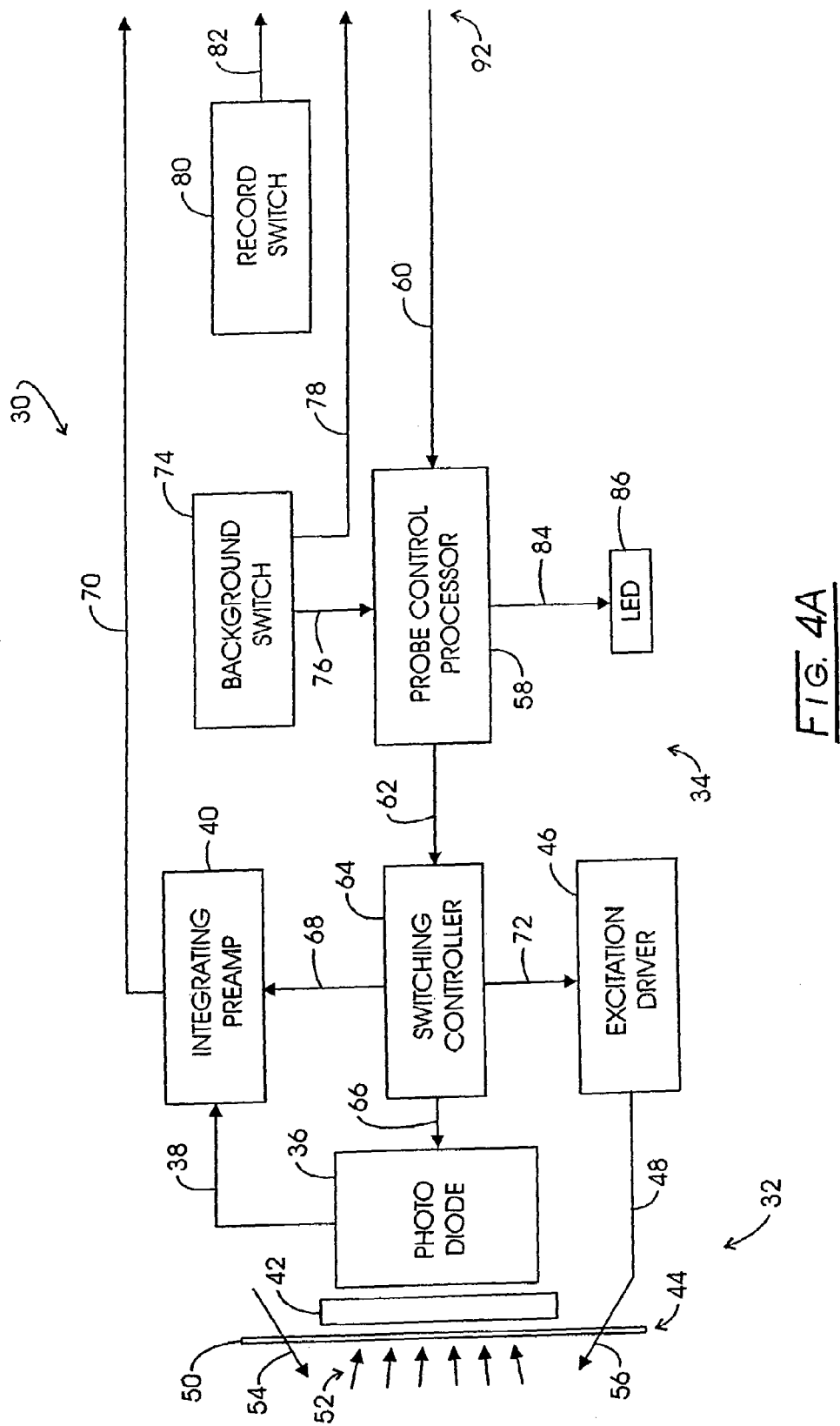
FIG. 4A is a block diagram showing the functional components of a probe suited for intra-operative use.
Figure 4B:
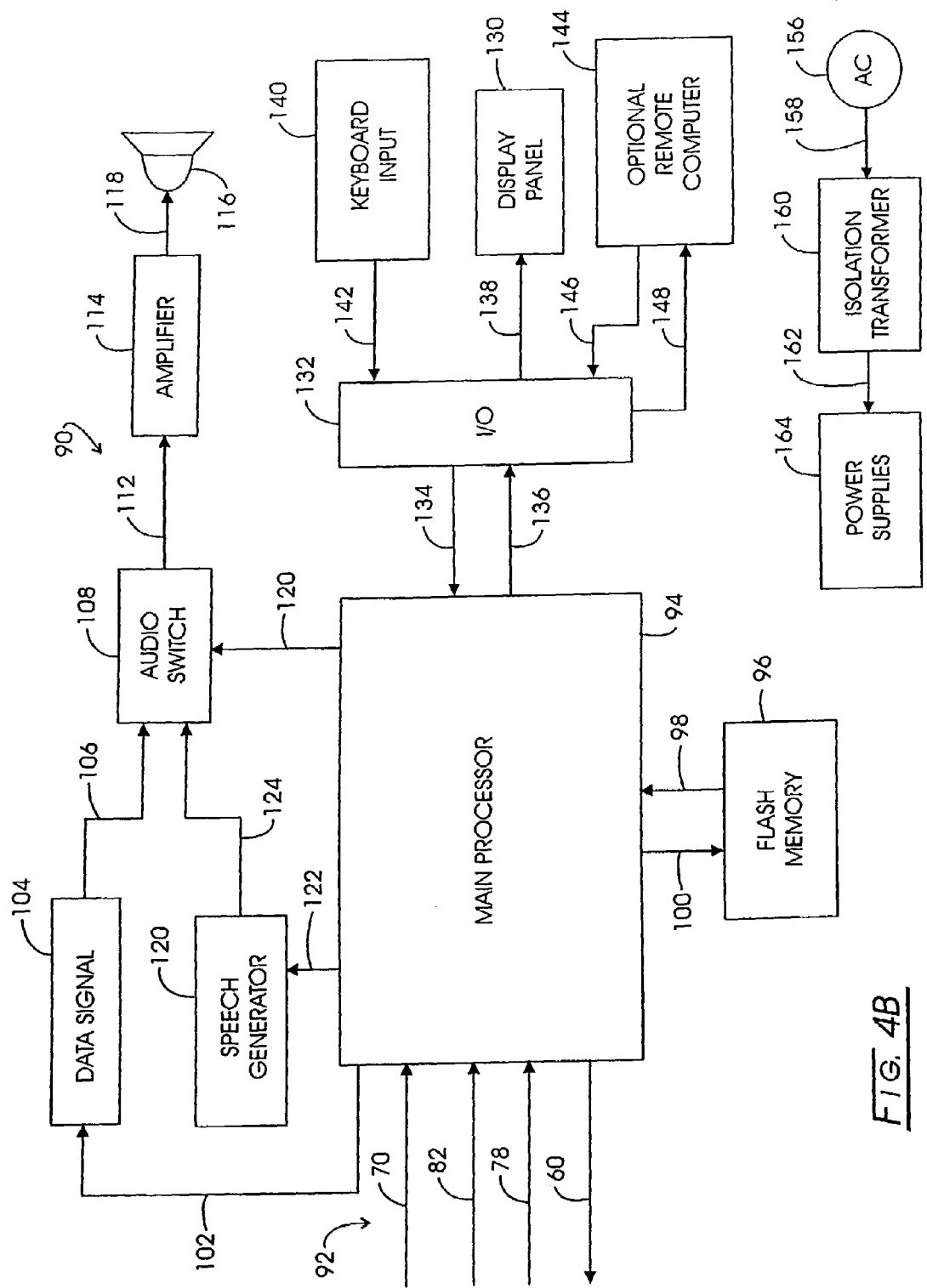
FIG. 4B is an extension of FIG. 4A and illustrates in block diagrammatic fashion the functional components of a control assembly.

FIGS. 4A and 4B combine to respectively represent the probe component of the system and a control console component of the system at hand. Looking to FIG. 4A, the functional components of the probe are represented in general at 30, the probe incorporating a working end, the components of which are represented in general at 32 and a support, the components of which are represented in general at 34. Looking to working end 32, a photo-detector, for example, a photodiode is represented at block 36 which performs in conjunction with an integrating preamplifier as represented at arrow 38 and block 40. Photodiode 36 may be provided, for example, as a type SD200-11-31-241, marketed by Advanced Photonix. Such devices may be obtained with an integrally retained preamplifier. Photodiode 36 is isolated from most of the ambient illumination, which may be encountered in an operating room theater as well as excitation wavelengths by a longpass filter represented at 42. Operating rooms are typically structured with very intense incandescent lighting, which will exhibit an infrared component. Filter 42 is intended to block substantially all (excitation and ambient) but those components, which may be accommodated for by initialization and modulation approaches to generating excitation illumination and enabling photodiode 36. Extending around the longpass filter 42 is an excitation assembly 44 including a mount and, for instance, an array of eight light emitting diodes, which may be provided, for instance, as light emitting diodes emitting in the red region of the spectrum (Lumex Surface Mount LED Digkey Part # 67-1727-1-ND). These excitation components are illuminated from an excitation driver network represented at block 46 as indicated by arrow 48. Securing the working end from body fluid contamination is a very thin transparent window represented at 50. The random, essentially homogenized fluorescing illumination is represented by the randomly oriented arrow array identified generally at 52. Preferably the excitation diodes are canted slightly inwardly to effect a red region illumination convergence. Arrows 54 and 56 represent such directionality. Excitation driver 46 may be located within support portion 34 of probe 30 along with such components as an optional local or probe control processor represented at block 58. Processor 58 is under the control of a main processor, which is console mounted and such control is represented at arrow 60. Local controller 58, as represented at arrow 62 asserts control over a switching controller represented at block 64 as represented at arrows 66 and 68. Controller 64 functions to enable photodiode 36, as well as integrating preamplifier 40. The output of the integrating preamplifier is directed to the console mounted main processor as represented at arrow 70. Controller 64 additionally asserts modulating control over the excitation driver 46 as represented at arrow 72.

Where the probe structure permits, support 34 may incorporate two switches, which are finger actuatable by the surgeon. In this regard, the support portion 34 may incorporate a background switch represented at block 74, which provides an input to the processor 58 as represented at arrow 76 as well as to the main processor as represented at arrow 78. By actuating switching 74, the amount of background fluorescing radiation which is not cancer involved may be assessed and from that information a statistically significant threshold fluorescing intensity level may be computed. The second switch, which may be mounted at the support 34, is a record switch as represented at block 80. Switch function 80 provides a switching signal directly to the main processor as represented at arrow 82. If actuated or held down for a short interval, the switch will cause a voice audio annunciation of an intensity level. Should switch 80 be held down for a longer interval, then a microphone is activated to permit the surgeon to comment as to the location, for example, of fluorescing nanocrystal material which has specifically bound a marker produced by or associated with neoplastic tissue. When such tissue is identified, the main processor will provide a cue, which preferably is audible. Such a cue may also be generated at the probe support 34 itself. For example, a visual cue may be provided by energizing a light emitting diode, as represented at arrow 84 and block 86.

Referring to FIG. 4B, the functional components of a control assembly associated with probe 30 are represented in block form. In the figure, arrows 70, 82, 78, and 60 reappear from FIG. 4A and are represented as being a component of an elongate flexible cable identified generally as at 92. These components of cable 92 extend to a main processor represented at block 94. Processor 94 performs interactively with flash memory represented at block 96, the interactive function being represented at arrows 98 and 100. Device 94 may be provided as a type STR 755 FVO marketed by S T Microsystems, Inc., of Geneva, Switzerland. As noted above, it may also perform the function of probe processor 58. In general, processor 94 will respond to an analog input as indicated at arrow 70 representing data derived from the integrating preamplifier 40 (FIG. 4A). That data will be digitized and evaluated with respect to the procedure being carried out. In this regard, during a scan mode of operation the incoming data will represent the intensity of fluorescence. That intensity will be statistically evaluated against measured background fluorescence developed from a scan of tissue wherein locator is not preferentially present. Where a statistically significant amount of evaluating fluorescent intensity is present, then as represented at arrow 102 and block 104, a numerical data signal is derived. As represented at arrow 106 and block 108, the signal may be directed to an audio switch under the control of processor 94 as represented at arrow 110. The signal at arrow 106 will then be transmitted as represented at arrow 112 to an amplifier represented at block 114. Amplifier 114 provides an audio signal to a loudspeaker 116 as represented at arrow 118. Such a signal audibly alerts the surgeon that the forward surface of the probe is over sufficient fluorescing locator, which will have specifically bound a marker produced by or associated with neoplastic tissue. During the era of the use of the RIGS system, the sound was referrer to as a "siren". The surgeon also may wish to hear a voice annunciation of the numeric level of intensity of fluorescence, which the probe is encountering. This can be carried out, for example, by actuating the record switch described at block 80 in connection with FIG. 4A. Note in this regard, the main processor is seen to be operationally associated with a speech generator as at block 120 as represented at arrow 122. As represented at arrow 124, the voice output of generator 120 is directed to audio switch 108, again under control of the main processor 94 as represented at arrow 110. The voice information then is directed to amplifier 114 as represented at arrow 112 and is outputted to loudspeaker 116 as represented at arrow 118. The fluorescence intensity related numerical data also may be displayed at a display panel represented at block 130. In this regard, main processor 94 is associated with an input/output (I/O) function represented at block 132 as indicated by arrows 134 and 136. Port 132 is shown operationally associated with display panel 130 by arrow 138. I/O port 132 also may be operationally associated with a keyboard input as represented at block 140 and arrow 142. It is also advantageous that the main processor 94 be capable of communication with a remote computer. Such an optional remote computer is represented at block 144 and the interaction with that computer via port 132 is represented at arrows 146 and 148.

Finally, power is supplied to the control assembly 90 as represented by an a.c. source, 156. As represented at arrow 158 and block 160, the a.c. source is directed to an isolation transformer and, in turn, as represented at arrow 162 and block 164 to control assembly power supply.

Referring to FIG. 5, a perspective view of the instant system is presented and identified in general at 170. Functions described in FIGS. 4A and 4B are identified in the instant figure with the same numeration. In this regard, control assembly 90 is identified in conjunction with a console 172 having a relatively large liquid crystal display again identified at 130. Display 130 provides numerical read-out of fluorescing intensities as well as a cueing to the operator particularly with respect to initialization procedures. Next to the display 130 is an audio grill 172 behind which a loudspeaker as earlier-described at 116 may be located. Cable 92 extends from a cable connector 174 to a probe again identified in general at 30 having a working end 32 and a support 34. Console 172 also is configured with a number of switches including an on/off toggle switch 176; record switch 178; a "squelch" switch 180; a calibration switch 182; an initialization 1 switch 184; an initialization 2 switch 186 and a two-position toggle switch 188 which functions to introduce the type of fluorescing nanocrystal employed, either a Type I or Type II. The term "squelch" as used herein became popular with practitioners of the earlier RIGS system and has a meaning somewhat different than given, for instance, in the authoritative dictionary of IEEE Standards Terms, $7^{th}$ Addition which gives the term two meanings (1) a circuit function that acts to suppress the audio output of a receiver when noise power that exceeds a predetermine level is present; or (2) facility incorporated in radio receivers to disable their signal output while the received carrier level is less than a preset value. In contrast, the squelch switch 180 is employed to develop a statistical fluorescing intensity value based upon a measured background fluorescing value. For example, with the instant procedure, the probe instrument 30 initially is positioned and scanned in the vicinity of a region not involved with cancer, for example, in the vicinity of the heart or aorta in order to obtain a blood pool background fluorescing intensity. The microprocessor 94 then calculates a statistically significant value, for example, a predetermined number of standard deviations of the mean background fluorescing intensity to derive a statistically significant threshold radiation count rate level.

In general, the console 172 will be located outside of the sterile field within a surgical theatre, while the probe instrument 30 will be within that sterile field and in the hand of a surgeon. As discussed in connection with FIG. 4A, it will be beneficial to afford the surgeon the opportunity to hand actuate the functions of switch 180, as described at 74 and switch 178 as described at 80 in FIG. 4A from the probe itself. The figure shows that the probe instrument 30 is configured having a generally cylindrical unitary housing 190 (support 34), which is hand graspable by the surgeon and is interactively associated with the console 172 via cable 92. Other forms of interactive transmission which are wireless may be employed in place of a cable as shown. The hand graspable support or unitary housing 190 extends from a forward end 192 and a rearward end 194. The term "unitary" is used herein to indicate that no joints or unions are present in the housing to establish a switching function. A working end 32 is coupled to the forward end 192 of housing 190 while the cable 92 is coupled at the rearward end 194. Two planar switch actuating surfaces are formed integrally into the housing 190 as shown at 196 and 198. Switches 196 and 198 carry out the functions described earlier respectively at 74 and 80. In this regard, surface 196 carries out a background or squelching function and the surface 198 carries out the above-discussed recording functions. Looking additionally to FIG. 6, it may be observed that surfaces 196 and 198 are machined into the housing 190 in a manner providing forwardly and rearwardly disposed bevels shown respectively at 200 and 202 which function, with the surfaces 196 and 198 to define a switching region 204. Intermediate the surfaces 196 and 198, a beveled rib 206 is defined having a flat, upwardly disposed surface 208 establishing a rib height which falls below the external periphery of housing 190. The thus defined switch region 204 is readily tactilely identifiable to the surgeon such that surface 196, carrying out the background function or squelch function of switch 180 is easily determined by the surgeon with respect to rib 206 and bevel 200. Similarly, the surgeon readily tactilely identifies the switch actuating surface 198 such that the functions of record switch 184 are easily determined by the surgeon with respect to rib 206 and bevel 202.

FIG. 6 reveals that the unitary housing 190 is configured having an internally disposed switch-receiving channel 210 which is open and accessible at the rearward portion of housing 190 through a cylindrical bore-formed cavity 212 as well as from a cylindrical bore-formed cavity of shorter length at the forward end as seen at 214. Channel 210 is accurately formed utilizing, for example, a wire electrical discharge machine (EDM). This permits a very accurate formation of an upwardly disposed switch contact surface 216 and a parallel planar oppositely disposed load surface 218. Each of the surfaces 216 and 218 and switch contact surface 216 is parallel with and spaced from switch actuating surfaces 196 and 198. A predetermined distance defining a switch wall 220 of thickness selected such that flexure at surfaces 196 and 198 under finger pressure is so minor as to be tactilely undetectable. For a preferred aluminum housing 190, that thickness will range from about 15 mils to 20 mils and resultant flexure upon switch actuation from surfaces 196 and 198 will be in a micro-inch range such that, in effect, the operator is transmitting hand generated stress with almost no accompanying material strain. Accordingly, sealing is achieved due to the unitary structure of the construction of housing 190 without the imposition of fatigue which otherwise might evoke the presence of cracks at switching region 204 to thus permit the ingress of body fluids into the internal regions of the probe instrument.

Positioned in abutting adjacency with switch contact surface 216 is the pressure responsive surface of a two-component thin piezoelectric switch 222. Such pressure responsive surface of the two-component switch 222 is supported from a stiff substrate, for example, formed of FR4 material. The bottom of this material is a flat oppositely disposed support surface, which incorporates three terminals (not shown). With the arrangement, one switching component is located directly beneath switch actuating surface 196 and the other directly beneath switch actuating surface 198. Switches as at 222 are marketed by Wilson-Hurd, Inc., of Wausau, Wis. and have been described, for example, in U.S. Pat. No. 4,857,887, issued Aug. 15, 1989. Preferably, such switches are preloaded in compression to enhance their performance.

To retain switch 222 compressively against the switch contact surface 216, a switch support assembly shown generally at 224 is provided. Assembly 224 is formed of two complimentary wedges 226 and 228 formed of aluminum with matching sloping surfaces which serve to provide oppositely disposed parallel outer surfaces between the load surface 218 and the bottom of switch 222. Transmission leads extend from the switch 222 to a printed circuit board 230 structurally and operationally supporting the components described in FIG. 4A. Circuit board 230 is also operationally coupled with cable 92 as represented at lead array 232. The switching structure shown was developed for utilization with the earlier-described RIGS system and is described at a higher level of detail in U.S. Pat. No. 5,682,888 by Olson and Thurston, entitled "Apparatus and System for Detecting and Locating Photon Emissions With Remote Switch Control", issued Nov. 4, 1997 and incorporated herein by reference.

Circuit board 230 also supports the earlier-described LED function 86. In this regard, an LED is represented at 234 positioned beneath a transparent polycarbonate plug 236 mounted within housing 190. Rearward end 194 of the housing 190 is connected to the necked down cylindrical portion 238 of a cylindrical rear cap 240. Rear cap 240 is intimately coupled with an elongate conically-shaped relief component 242 formed of a medical grade silicone, which surmounts and seals against cable 92.

Forward end 192 of the probe support 34 is canted at an angle of 15° with respect to probe axis 250. Attached to this forward end 192 is a short connector tube 252, the rearward end of which also is canted at a 15° angle with respect to axis 250. Connector tube 252 is connected to the housing 190 at end 192 to provide a desirable 30° cant for the working end 32. Looking additionally to FIG. 6A, an aluminum cylindrical cap 254 is attached to and extends over the forward portion of connector tube 252 and is seen to retain a transparent thin window 256 formed, for example, of polycarbonate with a thickness of 0.020 inch. FIG. 6A reveals that cap 254 is positioned to over and connected to a cylindrical extension with forward portion 258 of connector tube 252. Supported immediately against the interior surface of portion 258 is a generally cylindrical copper excitation mount which has a forward edge 262 which is inwardly beveled and functions to support an array of excitation diodes represented generally at 264. Looking additionally to FIG. 7, the array 264 is seen to comprise light emitting diodes 266a-266h. These diodes emit in the red region of the spectrum and each is surface mounted upon a printed circuit supported by a thin polyimide substrate or film sold under the trade designation "Kapton", by E.I. DuPont de Nemours and Company. The printed circuit is represented in FIG. 6A at 268. The Kapton is adhesively secured to the forward edge 262 of the excitation mount 260. Next inwardly from excitation mount 260 is a polymeric detection assembly mount 270. The outer surface of mount 270 is notched to direct dual leads from the LED associated printed circuit mounts to circuit board 230 (FIG. 6). Two such leads are seen in FIG. 6A at 272a and 272e. Mount 270 additionally is centrally bored to support a pre-amplification stage again represented at 40; a forward detector again identified at 36 and a longpass filter again identified at 42. Filter 42 functions to block the red region excitation illumination from the LED array 264 as well as essentially all ambient illumination. A preamplifier output is represented at lead pair 274, which also extends to printed circuit board 230 (FIG. 6). In general, LEDs as at 266a-266h will exhibit about a 2-volt drop, thus, with an adequate power supply, permitting them to be coupled in series circuit fashion.

In the course of carrying out initialization procedures it is necessary that the working end 32 of the probe be inserted within a light-tight chamber, preferably provided as a cup-shaped cap. Looking to FIG. 8, such a cylindrically shaped cap is identified in general at 280, the internal cavity defined thereby being seen at 282. Turning to FIG. 9, cap 280 reappears in section and is seen to incorporate a polymeric material 284, which is structured to emulate the excitation light scattering induced by human tissue. This particular cap is arbitrarily designated as cap A. An essentially identical cap, arbitrarily designated cap B will incorporate the fluorescing nanocrystal employed with the system. One such nanocrystal will correspond to the above-described Type I and a third cap, C, will incorporate nanocrystals identified above as Type II.

Referring to FIG. 10, a flow chart describing the initialization of the system in conjunction with cap A is set forth. Looking to that figure, a system power-up is represented at symbol 290 and arrow 292. Actuating toggle switch 176, as described in connection with FIG. 5, carries out this power-up. Under control of main processor 94 (FIG. 4B), the display 130 will prompt the operator to place cap A on the probe and press "INIT1" (switch 184) when ready. Next, as represented at arrow 294 and block 296, a query is made as to whether the INIT1 switch has been pressed. In the event it has not, then the system dwells as represented at loop arrow 298. Where the INIT1 switch has been pressed, then as represented at arrow 300 and block 302, a display will provide a prompt that excitation pulses are off and the photodiode is on. Additionally, it will advise that the system will read an average, n, pulses and store a resultant value as DARK CURRENT. The resultant value represents electronic noise and dark current in the photodiode. With such storage, then as represented at arrow 304 and block 306, a prompt is published at display 130 cueing the operator to press toggle switch 188 to elect a Type I or Type II nanocrystal incorporating locator. Accordingly, as represented at arrow 308 and block 310, the operator enters nanocrystal data, the election of Type I being represented at arrow 312 and the storage of that information being represented at block 314. Correspondingly, as represented at arrow 316 and block 318 where a Type II nanocrystal has been entered in the system via switch 188, then the system will store Type II.

Returning to block 314, where the nanocrystal at hand is Type I, then as represented at arrow 320 and block 322, the user is prompted to press INIT2 button 186 while cap A remains in place. This will cause the system to turn-on excitation pulses and synchronously enable or drive the photodetector 36. The result is a test of the longpass filter 42 with respect to scattered excitation light. Accordingly, as represented at arrow 324, arrow 326 and block 328, the system reads and averages, n, pulses from the photodiode 36. That value then is added to the DARK CURRENT value described in connection with block 302 and the result is stored as REFERENCE.

Where a Type II nanocrystal has been stored, then as represented at arrow 330 and block 332, the excitation pulses are turned on. However, the system provides a delay in the photodiode read pulses until after the end of the excitation pulses. It should be kept in mind that this is a test of the accuracy of longpass filter 42 with respect to excitation light. As represented at arrow 334, the system then carries out the procedure represented at block 326. The initialization then continues as represented at arrow 336 and node A.

Figure 11:
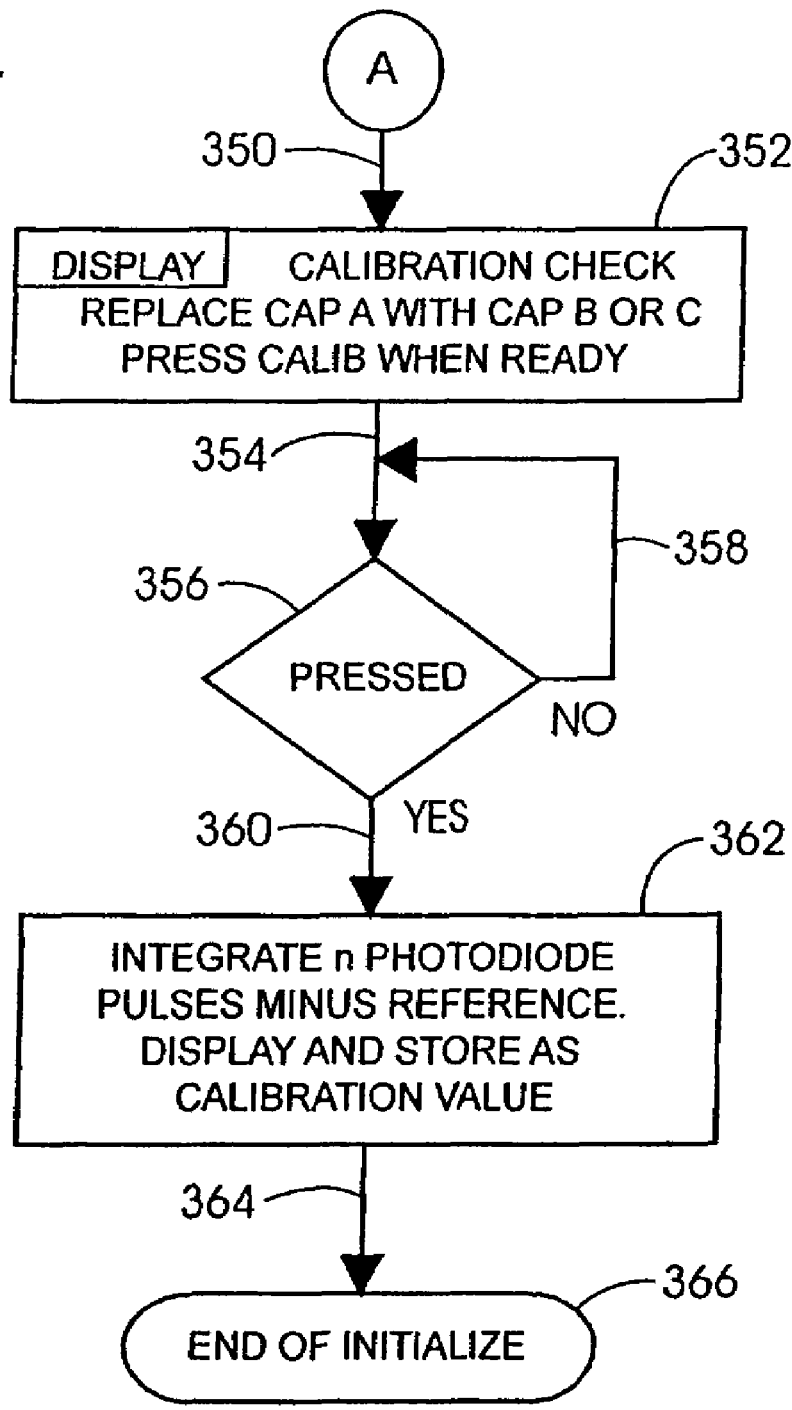
FIG. 11 is a flow chart illustrating an initialization procedure providing a calibration check of the system.

Referring to FIG. 11, node A reappears in conjunction with arrow 350 extending to block 352. As represented at block 352, a prompt is provided at display 130 calling for a calibration check to replace cap A with either cap B or cap C. Additionally, the operator is instructed to press the calibration switch (switch 182) when ready. Next, as represented at arrow 354 and block 356, a determination is made as to whether console switch 182 has been pressed. In the event that it has not, then as represented at loop arrow 358, the system dwells. However, when the switch button has been pressed, as represented at arrow 360 and block 362, the system integrates, n, photodiode pulses and subtracts REFERENCE. The result is displayed as a numerical fluorescence intensity value identified as "CALIBRATION VALUE". That number is then compared by the operator with a calibration number carried by cap B or cap C. Where those numbers are substantially the same, then the operator knows that the system is properly operating. As represented at arrow 364 and node 366, the initialization procedure then is completed.

In general, with the procedure at hand, the patient is administered an effective amount of a locator incorporating a fluorescing nanocrystals (or other fluorescing agent) and which specifically binds a marker produced by or associated with neoplastic tissue. Administration is by injection. Following the injection, a clearing time is permitted to elapse permitting the locator to preferentially concentrate at any marker and for unbound locator to be cleared from the body so as to increase the ratio of fluorescing-based radiation from specifically bound locator to fluorescing-based radiation representing background in the patient. In general, the clearing time is determined by the form of antibody or locator employed and typically will be from about two to about three weeks. Background determinations can be made in conjunction with blood tests. After the clearance time has elapsed, the patient is surgically assessed at an operative field. As the initial component of assessing the field, the above-described squelch procedure is carried out. Such a procedure was carried out during the era of RIGS where the radioisotope detecting probe would be held in stationary position such as at the aorta and background blood pool radiation values were determined. Because of the vascularity of tissue, with the instant system, squelch is undertaken with a scanning.

Figure 12:
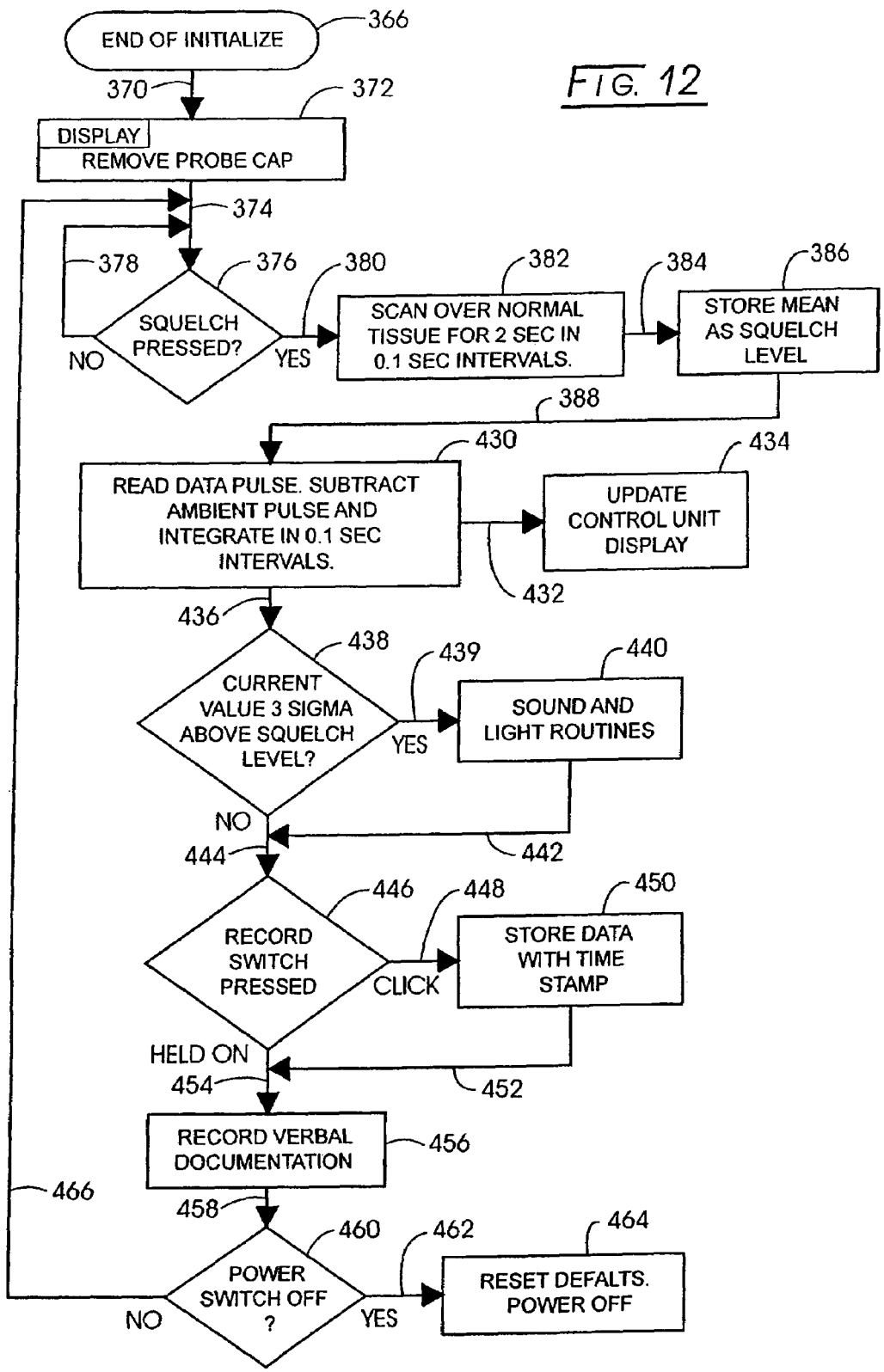
FIG. 12 is a flow chart illustrating a scan routine.

FIG. 12 is a flow chart illustrating scan routines employed with the system. Looking to the figure, node 366 reappears in conjunction with arrow 370 and block 372. Block 372 provides for a prompt at display 130 instructing the practitioner to remove the probe cap B or C. A further prompt instructing the practitioner to press the squelch button 180 may be published. Then, as represented at arrow 374 and block 376, a determination is made as to whether the squelch switch has been actuated. If it has not, then as represented by loop line 378, the system dwells. Where the squelch switch has been actuated, then as represented at arrow 380 and block 382 the practitioner, using the probe, scans over normal tissue for two seconds in repeating 0.1-second sampling intervals. A resulting fluorescing intensity data is treated to derive a mean value and, as represented at arrow 384 and block 386, that mean value is stored as SQUELCH LEVEL and the procedure continues as represented at arrow 388.

Figure 13:
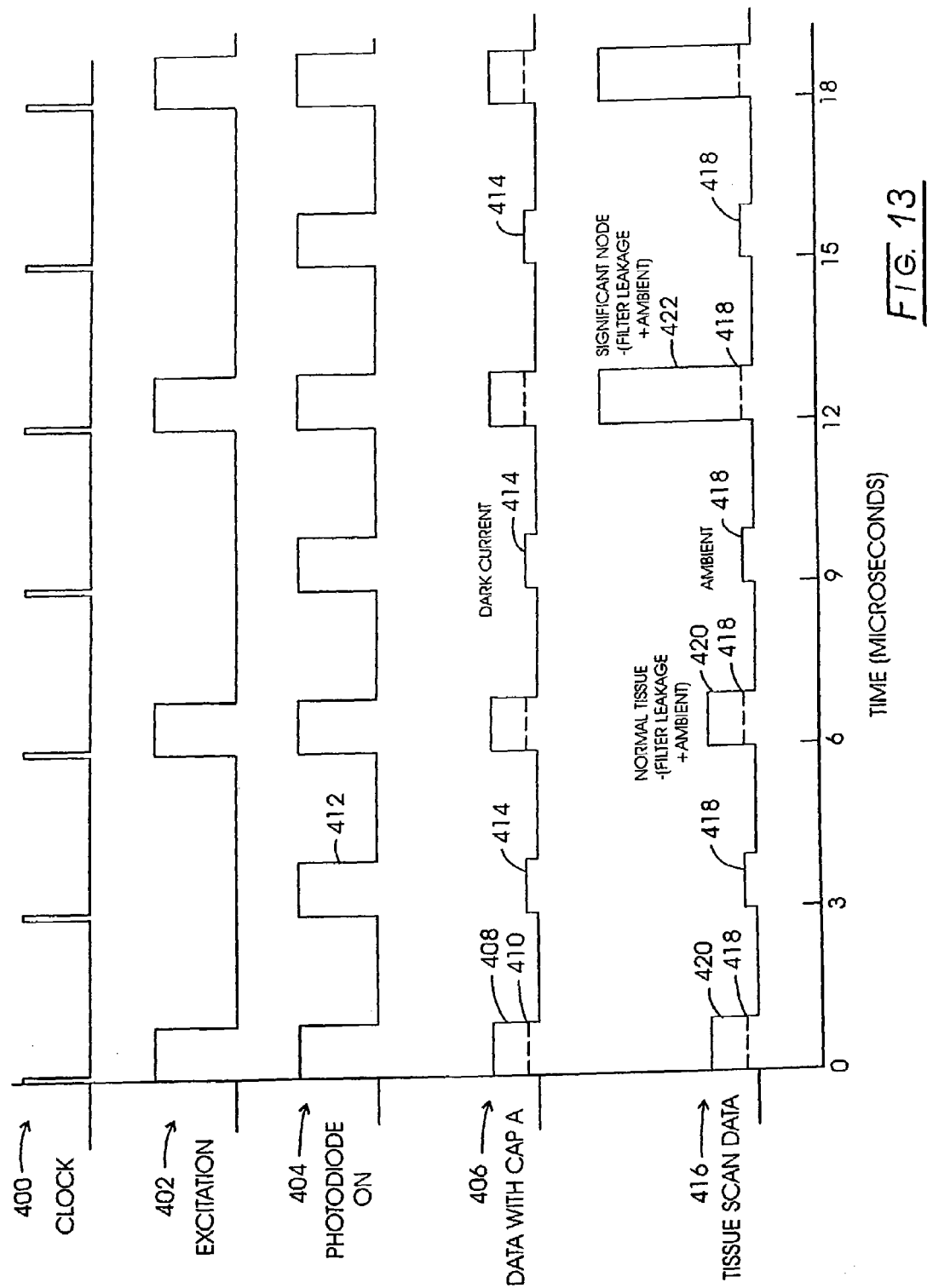
FIG. 13 is a timing diagram illustrating a pulse-based procedure for utilization with Type I nanocrystal.

Looking momentarily to FIG. 13, a timing diagram corresponding with the utilization of a Type I nanocrystal-based locator is provided. The diagram shows time in microseconds and modulation carried out with clock pulses as represented at diagram 400. In the figure, amplitudes are arbitrary and excitation pulses as well as enablement of the photodiode are again arbitrarily established as one microsecond. In this regard, the excitation pulses are represented at diagram 402 and the enablement or driving of the photodiode is represented in general at 404. In this regard, for a Type 1 nanocrystal, the photodiode is enabled in synchronization with the energization of the excitation components. Diagram level 406 in FIG. 13 represents initialization data obtained with cap A installed. In this regard, as shown at amplitude 408 data obtained with cap A installed shows a filter test amplitude at 408 with a combined DARK CURRENT evaluation represented at dashed line level 410. That level 410 is obtained by enabling the photodiode as shown at 412 and reading DARK CURRENT as shown at 414. At level 416 of FIG. 13, tissue scan data is presented, amplitudes 408 and 410 reappearing but additionally, an amplitude is shown at 418 which represents a condition wherein the excitation diodes are not energized but the photodiode is enabled or driven. This amplitude is categorized as "ambient amplitude". In the course of utilization of the probe, the user may alter its forward surface orientation with respect to the tissue being scanned. This may admit some ambient illumination including the earlier-described steady-state infrared illumination from the incandescent lighting of the operating room. Note that the data representing amplitude 418 is collected with the photodiode on as represented at 412 and the excitation diodes are off. When the probe is scanning over normal or unaffected tissue an amplitude, for example, as shown at 420 may be encountered which will be considered to be statistically insignificant, for example, being less than three standard deviations over the mean squelch level developed as represented at block 386 in FIG. 12. In effect, amplitude 420 will represent detected fluorescence from which the sum of the leakage of filter 42 and any ambient illumination is subtracted. Amplitude 422 represents the positioning of the probe forward surface against a tissue location wherein the fluorescing radiation intensity is at a level, which is statistically significant and the system generates a perceptible cue. It will be beneficial to periodically compare the level 418 of ambient illumination with SQUELCH LEVEL and alert the practitioner with respect to any ambiguity showing a higher than anticipated ambient illumination level.

Returning to FIG. 12, arrow 388 is seen to be directed to block 430, which provides for the reading of a data pulse and the subtraction of the ambient pulse, the initialization corrections having been accommodated for. Integration of the data pulse as corrected occurs in 0.1 second intervals, to provide a fluorescing intensity level as corrected data output which, as represented at arrow 432 and block 434 is displayed at display 130. Where the user wishes to determine the displayed value, then the report switch 80 is momentarily depressed to evoke a voice transmission of the number representing fluorescing intensity. This data is treated by the control assembly as represented at arrow 436 and block 438 where an analysis is made as to whether the corrected data is of a value representing three standard deviations above SQUELCH LEVEL. A three-sigma criterion for significance is selected because the expected probability of a false positive reading would be less than 1% for such an analysis. Where that criteria of statistical significance is met, then as represented at arrow 438 and block 440 the system generates a sound at loudspeaker 116 and illuminates light emitting diode 86. At this point of the procedure, the surgeon may wish to depress the record switch 80 for an extended interval to activate a microphone and record the location of this locator concentration. It also should be pointed out that the surgeon generally will have removed readily discernable neoplastic tissue, which will have been located by external imaging systems as well as by observation and palpation. However, where lymph nodes are involved, such detection techniques are not available and essentially only an intra-operative probe-based system will locate the cancer involved lymph nodes.

From block 440 the procedure continues as represented at arrows 442 and 444 to the query posed at block 446 determining whether the record switch 80 has been actuated. In the event that it has been actuated for a short interval or in a "click" manner, then as represented at arrow 448 and block 450, the fluorescing intensity data is stored in conjunction with a time stamp. The procedure then continues as represented at arrows 452 and 454. Looking particularly to arrow 454 where the record switch is held on by the surgeon, then a microphone is activated and the surgeon may comment upon the activity then being undertaken. For example, identifying the location of a removed lymph node as represented at block 456 and verbal documentation is recorded. Arrow 458 extends from block 456 to the query at block 460 determining whether the power switch has been turned to an off position. In the event that it has, then as represented at arrow 462 and block 464, all defaults are reset and power is terminated. In the event of a negative determination at block 460, then as represented at arrow 466, the procedure reverts to arrow 474.

Figure 14:
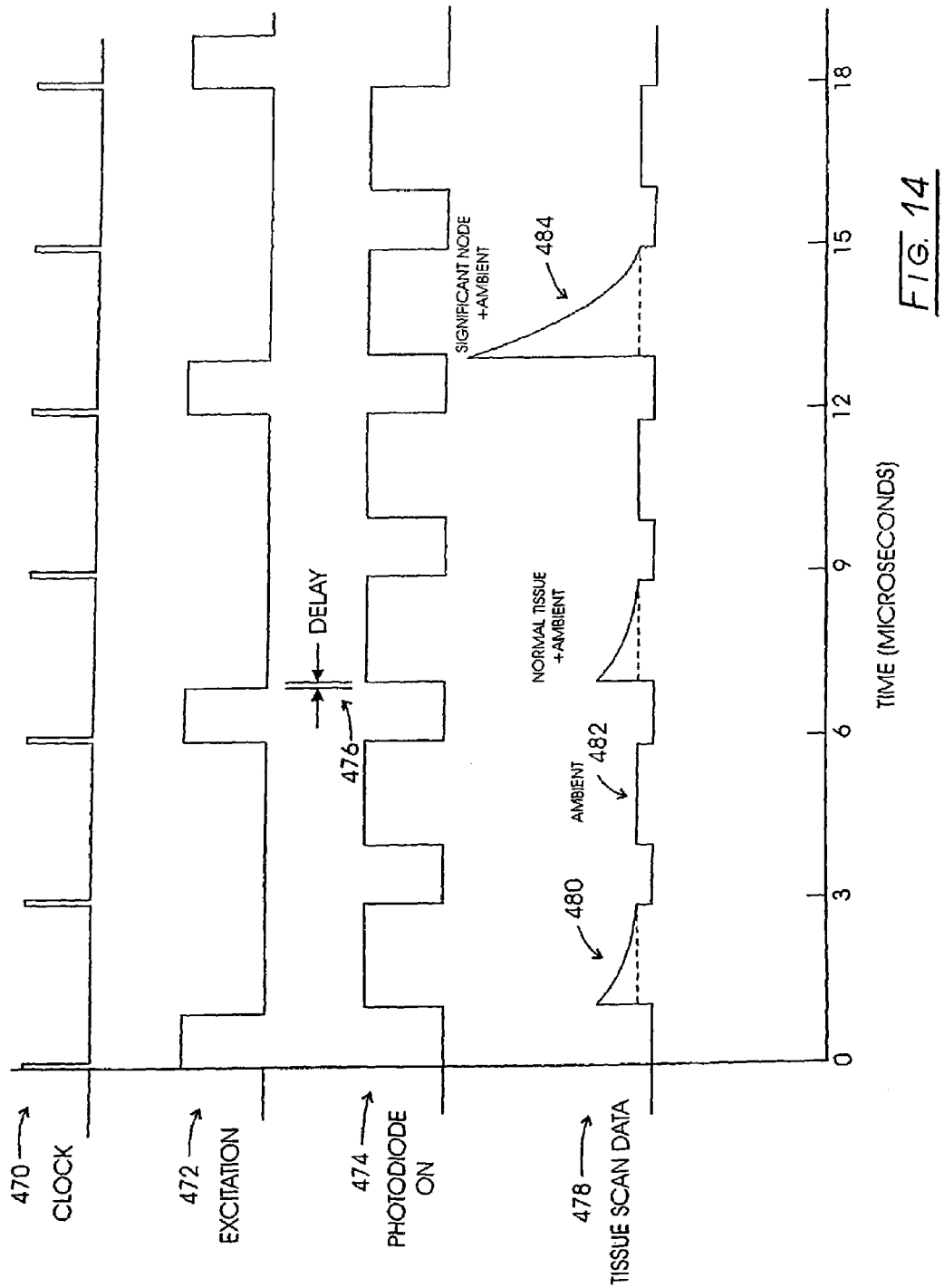
FIG. 14 is a timing diagram showing a pulse-based method utilized in conjunction with Type II nanocrystal.

Referring to FIG. 14, a timing diagram is provided concerning the use of a Type II fluorescing nanocrystal and locator combination. In the figure, clock pulses are indicated at level 470, while excitation pulses are represented at level 472. In this regard, excitation is seen to occur for a microsecond interval. The enabling or driving of photodiode 36 is represented at level 474. Such enablement occurs about 10 nanoseconds following the termination of the excitation pulse as represented in general at 476. It may be recalled that when a photon of excitation is absorbed by a fluorescing nanocrystal of this type, the emitted photon has a random delay time or time constant that is of the order of a microsecond. Thus, if the modulation of the excitation has the form of short pulses, the fluorescence will continue after the excitation has stopped. To use this effect and eliminate the effect at the photodiode occasioned by scattered excitation energy, the reading pulse is started a short time after the excitation pulse has ended. Resultant tissue scanned data is represented at timing diagram level 478. At that level, for example, at reading interval 480 occasioned when the probe is over normal tissue the data will represent a combination of ambient illumination and an exponential decay of fluorescence, it being recalled that fluorescence also will occur during the excitation interval. As before, ambient illumination is measured as shown at reading 482, which occurs with the photodiode in an enabled condition and with the absence of excitation energy. Where the frontal surface of the probe is over a statistically significant region of locator, the exponential decay will be from a higher level as represented at reading 484. Computation of the total fluorescence intensity is computed by convolution procedure.

Probes employed with the instant system and method may be provided with configurations other than that shown and described in connection with FIGS. 5, 6, 6A and 7. One alternative approach is to configure the probe such that it will be slideably positioned upon a finger of the surgeon. This is quite helpful in maintaining a proper orientation of the probe with respect to tissue being scanned, particularly in hard to access areas. Referring to FIG. 16, a "finger probe" assembly is represented generally at 490 as it is carried by a surgeon represented schematically at 492. The probe component of the assembly 490 is shown at 494 being slideably mounted on the second finger 496 of the hand 498 of surgeon 490. Probe component 494 is represented as being in an active detection position such that it is mounted over the portion of finger 496 corresponding with one phalanx bone (connected to the tip phalanx), although location beneath the glove has been contemplated. It may, of course, be used on a different finger at the surgeon's discretion. As is apparent, the component 494 is located outwardly of the surgeon's glove and further extending outwardly of the glove is an initial length of communicating cable or wiring 500 which extends a limited distance along the forearm 502 of surgeon 490, whereupon it is secured by a strap 504 in the vicinity of the elbow joint. It then is seen to extend to the shoulder region 506 of surgeon 490 at which position a circuit housing 508 is fastened to the surgeon's arm, for example, by a strap or connector 510. With the exception of switches 74 and 80, the housing 508 may include the electronic components described in connection with FIG. 4A. Additionally, a second pre-amplification stage may be incorporated within circuit housing 508. From the circuit housing 508 a cable 510 as described at 92 earlier herein may extend to a console as described at 172 in FIG. 5.

In FIG. 15, the "back" side of probe 494, which is an elastomeric strap, is seen. Looking to FIG. 16, the opposite side of this probe component 494 is revealed. Shown in FIG. 16 as being mounted at or near the tip of the underside of the finger 496, the length of probe 494 along finger 496 is about 2 cm. This short length permits retention of the device while allowing finger flexure. Probe component 494 carries non-imaging optical components configured in the same manner described in connection with FIGS. 6, 6A and 7. Those components are represented in general in FIG. 16 at 514. Where the component 494 is not in active use, the surgeon may simply rotate it about finger 496 to the topside of hand 498.

Looking to FIG. 17, the probe component 494 is shown in perspective. Component 494 may be formed, for instance, from aluminum or plastic and is configured having a finger mount represented generally at 516 which includes a support region 518 and an oppositely disposed concave mount portion 520. Support portion 518 carries the probe working end non-imaging optics including a transparent polycarbonate window, a cylindrical copper excitation mount and heat sink, longpass filter, photodiodes and associated preamplifier. In the figure, the transparent window is seen at 522, covering the probe top, an array of eight light emitting excitation diodes is represented in general at 524 and a longpass filter is represented at 526 behind window 522.

FIG. 17 reveals that the outward surface of the concave mount portion 520 is configured in concave fashion to develop an elongate guideways 528 and 530 extending along the lengthwise extent of the component 494. These guideways 528 and 530 aid in maintaining and changing the orientation of the probe component 494 through their abutting contact with adjacent fingers of the surgeon's hand. The internal region of the concave mount portion 520 is configured substantially as a half cylindrical surface 532 of radius selected for nesting against the surgeon's mounting finger. This surface 532 extends to two oppositely disposed strap connector portions 534 and 536, each of which is formed as an elongate slot. These connector portions 534 and 536 serve to provide for the attachment of an elastomeric web-like strap 538 which functions to retain the finger mount against the surgeon's hand and exhibits sufficient flexure or elasticity so as to permit the movement of the probe component about the finger.

FIG. 18 looks to a sectional view of the probe 494, which includes the upper cap-shaped transparent polycarbonate window 522. Immediately adjacent the central portion of window 522 is longpass filter 526, which extends over the outwardly facing surface of photodiode 542, which is operationally combined with a preamplifier 544. Surrounding this assemblage in the manner described in FIG. 6A is a cylindrical copper heat sink and excitation component support 546. The forward edge of support 546 is canted inwardly to cause the excitation outputs of the array of excitation light emitting diodes 524 to converge as represented by dashed lines 548 and 550. Additionally as in the case of FIGS. 6 and 6A, the light emitting excitation diodes are mounted upon a thin Kapton (polyimide) carried printed circuit, the leads from which extend to cable 500 as well as the leads extending to and from pre-amplification stage 544. Polymeric support material 552 is shown supporting the detector components as well as transparent window cap 522.

A similar finger probe was developed for utilization with the RIGS system involving the detection of radioisotope. That implementation for the RIGS system is described in detail in U.S. Pat. No. 5,441,050 by Thurston and Olson, issued Aug. 15, 1995, entitled "Radiation Responsive Surgical Instrument" and incorporated herein by reference.

The probe detector components of the present system also may be adapted to utilization in the course of laparoscopic surgery. From a laparoscopic surgical standpoint, it is necessary that the laparoscopic instrument be maneuverable, having an access tube of a diameter limited by the port of a cannula, for example, less than 12 mm. Experience with the RIGS system has shown that the detection component of such an instrument should be "side looking". In this regard, the forward transmission surface of the detector components should be parallel with the axis of the instrument. As the detection component of the instrument is maneuvered within the insufflated body cavity, it is observed in real-time two dimensionally with a television camera, which also is inserted through a cannula into the body cavity.

Referring to FIG. 19, a laparoscopic instrument identified generally at 560 is represented in perspective. The working end of instrument 560 is shown in general at 562. End 562 is coupled to a support, which now comprises an elongate accessing tube 564, which, in turn, is coupled with a hand graspable handle 566. Extending from handle 566 is a cable again identified at 92, which is coupled to a cable receptacle 174 of a console 172 (FIG. 5). Accessing tube 564 will have a length of about 14 inches (36 cm) and a diameter of 11 mm permitting its insertion through a 12 mm diameter cannula. The transmission surface of working end 562 is shown at 568. As described in connection with FIG. 4A, handle 566 may incorporate a background or squelch switch 74; a record switch 80 and an LED 86 which functions as a cue representing the detection of a statistically significant amount of fluorescing radiation. As discussed earlier, that cue can be combined with an audible cue emanating from the console 172.

Looking to FIG. 20, working end 562 is revealed at an enhanced level of detail in conjunction with instrument axis 570. Detector structuring is seen to be quite similar to that described in connection with FIG. 6A. In this regard, a longpass filter is shown at 572 in immediate adjacency with a transparent polycarbonate window 574, the outer surface of which constitutes a transmission surface. Immediately beneath the longpass filter 568 is a photo-detector 576, which is combined with a preamplifier 578. A polymeric support 580 surrounds and supports components 572, 576 and 578 and provides a cylindrically shaped outer surface against which a copper excitation component support and heatsink 582 is mounted. The upwardly disposed edge of copper support 582 is canted inwardly and, in turn, supports a polyimide (Kapton) substrate carrying a printed circuit to which an array 584 of red region light emitting diodes (LEDs) is mounted. With such an arrangement, a converging red region excitation energy is generated as represented at dashed lines 586 and 588. Looking momentarily to FIG. 21, the LED array 584 is revealed as it is present beneath transparent window 574. These excitation LEDs are identified at 588*a*-588*h*. Recalling that the widthwise extent of the working end is 11 mm, the arrangement illustrated in FIG. 21 is acceptable. The LEDs, for example, will have a rectangular ceramic substrate having a width of 0.8 mm and a length of 1.6 mm.

Returning to FIG. 20, it may be observed that non-imaging optical components as well as preamplifier 578 are mounted upon a printed circuit board 590, which additionally is coupled with multi-strand leads 592 and 594 extending to handle 566. The printed circuit board assemblage in turn is mounted within a channel-shaped cradle 596 to which polymeric spacers as identified at 598 are adhesively attached. The fluid-tight union between working end 562 and accessing tube 564 is shown at 600. In view of the length of accessing tube 564, a supplementary pre-amplification stage may be incorporated within handle 566.

Transparent window 574 is seen to extend over the substantial flat portion of working end 562. Inasmuch as red excitation spectral energy is transmitted through it, a small portion of that energy will be light piped along it to enhance its visibility by a television camera.

Thurston, et al., entitled "Radiation Responsive Laparoscopic Instrument" describe the laparoscopic probe designed for utilization with the earlier RIGS system, issued Jul. 4, 1995.

Since certain changes may be made in the above-described method, system and apparatus without departing from the scope of the disclosure herein involved, it is intended that all matter contained in the description thereof or shown in the accompanying drawings shall be interpreted as illustrative and not in a limiting sense.

We claim:

1. A method for the surgical treatment of patients afflicted with neoplastic tissue, which comprises the steps:
   (a) administering to a patient an effective amount of a locator incorporating a fluorescing tracer and which specifically binds a marker produced by or associated with neoplastic tissue;
   (b) permitting time to elapse following step (a) for said locator to preferentially concentrate at any said marker and for unbound locator to be cleared so as to increase the ratio of fluorescing-based radiation from specifically bound locator to fluorescing-based radiation representing background in said patient;
   (c) after said time has elapsed in step (b) surgically accessing an operative field of the patient;
   (d) providing a hand manipulative probe having forwardly disposed excitation components energizable to cause any said fluorescing tracer to fluoresce at a detection wavelength or wavelengths and a forwardly disposed photo-detector configured for response to non-imaged said detection wavelengths so as to develop detection outputs corresponding with fluorescing radiation intensity;
   (e) using said probe, determining and storing the fluorescing radiation intensity at said background;
   (f) based upon the fluorescing radiation intensity at said background, determining a statistically significant fluorescing radiation intensity value whereat a perceptible cue is generated;
   (g) removing tumor burden from the patient using the probe where necessary to locate and differentiate neoplastic tissue; and
   (h) using the probe, determine and remove lymph tissue sites exhibiting detection outputs.

2. The method of claim 1 in which:
   step (a) administers said locator wherein a fluorescing nanocrystal is configured to fluoresce in the near infrared region of the spectrum.

3. A probe configured for detecting fluorescing tracers at the body, the tracers being responsive to wavelength defined excitation energy to fluoresce at one or more detection wavelengths including the near-infra-red region of the spectrum, comprising:
   a working portion having a transparent window with a forward transmission surface generally contactable with tissue of the body;
   a photo-detector disposed generally centrally and rearwardly of said window and configured for response to non-imaged fluorescing-based radiation;
   a generally cylindrical excitation mount within said working portion having a forward edge symmetrically disposed in spaced adjacency from said photo-detector;
   an array of excitation diodes supported at said mount forward edge in adjacency with said window, energizable under a modulation scheme to project photon excitation energy at an excitation wavelength or wavelengths through said window;
   a longpass filter located intermediate said photo-detector and said window configured to substantially block excitation and ambient illumination;
   an integrating pre-amplifier located rearwardly of said photo-detector and electrically coupled therewith to amplify a value associated with said non-imaged fluorescing-based radiation of its output to provide a pre-amplified detection output; and
   a support for supporting said working portion.

4. The probe of claim 3 in which:
   said excitation mount forward edge is inwardly beveled to orient the excitation diodes to project photon excitation energy in a manner generally mutually converging at an effective tissue penetrating distance in front of said window.

5. The probe of claim 4 in which:
   said excitation mount is formed of a thermally conductive material effective to provide a heat sink function.

6. The probe of claim 5 further comprising:
   a thin, electrically insulative polymeric substrate supporting a printed circuit upon which said excitation diodes are coupled electrically and structurally for being electrically energized, mounted upon said forward edge.

7. The probe of claim 3 further comprising:
   a probe control processor within said support;
   a excitation driver within said support controllable to energize said excitation diodes; and
   switching controller within said support under the control of said probe control processor and controllable to enable said photo-detector and integrating preamplifier and control said excitation driver.

* * * * *